United States Patent
Mei

(10) Patent No.: US 9,765,382 B2
(45) Date of Patent: Sep. 19, 2017

(54) APPLICATION OF RUTHENIUM COMPLEXES AS NUCLEIC ACID VECTORS OF TARGET CELL NUCLEUSES

(71) Applicant: Guangdong Pharmaceutical University, Guangzhou (CN)

(72) Inventor: Wenjie Mei, Guangzhou (CN)

(73) Assignee: Guangdong Pharmaceutical University, Guangzhou (CN)

( * ) Notice: Subject to any disclaimer, the term of this patent is extended or adjusted under 35 U.S.C. 154(b) by 0 days.

(21) Appl. No.: 15/059,565

(22) Filed: Mar. 3, 2016

(65) Prior Publication Data

US 2017/0056525 A1    Mar. 2, 2017

(30) Foreign Application Priority Data

Sep. 2, 2015  (CN) .......................... 2015 1 0559959

(51) Int. Cl.
*C09B 57/00* (2006.01)
*C12Q 1/68* (2006.01)
*C07F 15/00* (2006.01)
*C12N 15/87* (2006.01)

(52) U.S. Cl.
CPC ............ *C12Q 1/68* (2013.01); *C07F 15/0053* (2013.01); *C09B 57/00* (2013.01); *C12N 15/87* (2013.01)

(58) Field of Classification Search
None
See application file for complete search history.

(56) References Cited

PUBLICATIONS

Augustyn et al., 46(22) Inorganic Chemistry 9337-9350 (2007) (CAS Abstract).*

* cited by examiner

*Primary Examiner* — Timothy R Rozof
(74) *Attorney, Agent, or Firm* — Lowenstein Sandler LLP

(57) ABSTRACT

The present invention discloses an application of ruthenium complexes as nucleic acid vectors into target cell nucleuses. Experimental data shows that ruthenium (II) complexes may be effectively combined with nucleic acid sequence and may effectively change morphologies of long nucleic acid sequences to effectively deliver the nucleic acids into viable cells via transmembrane transport located within cell nucleuses, thus greatly improving transport efficiency of the nucleic acids. Based on this property, nucleic acid sequences can be conveniently transported into cells for gene therapy or fluorescent tracking or the like. The method for preparing a ruthenium coordination complex-nucleic acid complex in accordance with the present invention may provide a more effective and stable ruthenium coordination complex-nucleic acid complex.

14 Claims, 13 Drawing Sheets

A　　　　　　　　　　　　　B

A　　　　　　　　　　　　　B

A          B

A          B

A          B

A              B

A              B

A              B

A                                B

A                                B

A                                B

A          B

A          B

A          B

A          B

A                           B

A                           B

A                           B

A                           B

A　　　　　　　　　　　　　B

A　　　　　　　　　　　　　B

A　　　　　　　　　　　　　B

A　　　　　　　　　　　　　B

A    B

A    B

A    B

A    B

A             B

A             B

A             B

A             B

SEQUENCE LISTING

<160> NUMBER OF SEQ ID NOS: 8

<210> SEQ ID NO 1
<211> LENGTH: 22
<212> TYPE: DNA
<213> ORGANISM: Artificial Sequence
<220> FEATURE:
<223> OTHER INFORMATION: the sequence is synthesized

<400> SEQUENCE: 1
tgagggtggg gagggtgggg aa          22

<210> SEQ ID NO 2
<211> LENGTH: 27
<212> TYPE: DNA
<213> ORGANISM: Artificial Sequence
<220> FEATURE:
<223> OTHER INFORMATION: the sequence is synthesized

<400> SEQUENCE: 2
cgggcgcggg aggaaggggg cgggagc          27

<210> SEQ ID NO 3
<211> LENGTH: 21
<212> TYPE: DNA
<213> ORGANISM: Artificial Sequence
<220> FEATURE:
<223> OTHER INFORMATION: the sequence is synthesized

<400> SEQUENCE: 3
gggagggcgc tgggaggagg g          21

<210> SEQ ID NO 4
<211> LENGTH: 32
<212> TYPE: DNA
<213> ORGANISM: Artificial Sequence
<220> FEATURE:
<223> OTHER INFORMATION: the sequence is synthesized

<400> SEQUENCE: 4
gcggtgtggg aagagggaag aggggggaggc ag          32

<210> SEQ ID NO 5
<211> LENGTH: 26
<212> TYPE: DNA
<213> ORGANISM: Artificial Sequence
<220> FEATURE:
<223> OTHER INFORMATION: the sequence is synthesized

<400> SEQUENCE: 5
ggtggtggtg gttgtggtgg tggtgg          26

<210> SEQ ID NO 6
<211> LENGTH: 22
<212> TYPE: RNA
<213> ORGANISM: Artificial Sequence
<220> FEATURE:
<223> OTHER INFORMATION: the sequence is synthesized

<400> SEQUENCE: 6
uagcuuauca gacugauguu ga          22

```
<210> SEQ ID NO 7
<211> LENGTH: 18
<212> TYPE: RNA
<213> ORGANISM: Artificial Sequence
<220> FEATURE:
<223> OTHER INFORMATION: the sequence is synthesized

<400> SEQUENCE: 7
agauuagucu ccaucaua                                        18

<210> SEQ ID NO 8
<211> LENGTH: 6
<212> TYPE: DNA
<213> ORGANISM: Artificial Sequence
<220> FEATURE:
<223> OTHER INFORMATION: the sequence is synthesized

<400> SEQUENCE: 8 ttaggg                                                      6
```

APPLICATION OF RUTHENIUM COMPLEXES AS NUCLEIC ACID VECTORS OF TARGET CELL NUCLEUSES

TECHNICAL FIELD OF THE INVENTION

The invention relates to a novel application of ruthenium complexes, especially to a novel application of ruthenium complexes as nucleic acid vectors.

BACKGROUND OF THE INVENTION

Gene therapy techniques used in treating diseases, such as tumors, have increasingly drawn attentions and concerns of a large number of researchers. Gene therapy means transfecting some functional genetic materials, including siRNA, mRNA, miRNA, DNA, nucleic acid aptamers and promoter region sequences of cancer genes, into cells and expressing them in the cells to ultimately treat diseases. A key factor of gene therapy is to transfect therapeutic genes into cells by using safe and efficient vectors. Generally, viral vectors such as RNA viruses or DNA viruses, or non-viral vectors such as calcium phosphate precipitation, lipofection or microinjection and the like, are used to transfect therapeutic genes (H. Yin, R. L. Kanasty, A. A. Eltoukhy, A. J. Vegas, J. R. Dorkin, D. G. Anderson, Non-viral vectors for gene-based therapy, Nature Rev., 15, 541-555, 2014; Viktoriya Sokolova and Matthias Epple, Inorganic Nanoparticles as Carriers of Nucleic Acids into Cells, Angew. Chem. Int. Ed. 2008, 47, 1382-1395; S. Huo, S. Jin, X. Ma, X. Xue, K. Yang, A. Kumar, P. C. Wang, J. Zhang, Z. Hu, X.-J. Liang, Ultrasmall gold nano particles as carriers for nucleus-based gene therapy due to size-dependent nuclear entry, ACS NANO, 8(6), 5852-5862, 2014). However, due to their defects and deficiencies, clinical uses of these methods are still greatly limited.

In recent years, the study of using ruthenium (II) complexes as gene vectors has aroused widespread interests of many researchers. Kumbhar et al reported an application of ruthenium polypyridine complexes as gene vectors (S. S. Bhat, A. S. Kumbhar, A. K. Kumbhar, A. Khan, P. Lonnecke, Ruthenium(II) polypyridyl complexes as carriers for DNA delivery, Chem. Comm, 2011, 47, 11068-1070); Chao Hui et al reported a method of using ruthenium (II) polypyridyl complexes as gene vectors ( ). However, the ruthenium complexes used in these reports have relatively large molecular weight with relatively complicated synthesis processes, and have limited effects when used as gene vectors. Additionally, none of the above reports on ruthenium complexes and their optical isomers related to their use as gene vectors of target cell nucleuses. Replication and transcription of genes mainly takes place in cell nucleuses and the efficiency of self-replication and transcription of genes can be improved by nucleic acid-targeted delivery to cell nucleuses, thereby obtaining better therapeutic effects.

SUMMARY OF THE INVENTION

One object of the invention is to provide an application of ruthenium complexes as nucleic acid vectors.

Experimental data shows that ruthenium (II) complexes having the following general formula may be effectively combined with nucleic acid sequence to change the morphologies of the long nucleic acid sequence (e.g., more than 50 base pairs) and effectively deliver the nucleic acids into viable cells via transmembrane transport located within cell nucleuses, thereby greatly improving transport efficiency of the nucleic acids. Based on this property, nucleic acid sequences can be conveniently transported into cells for gene therapy or fluorescent tracking, etc.

The ruthenium (II) complex has the following general formula:

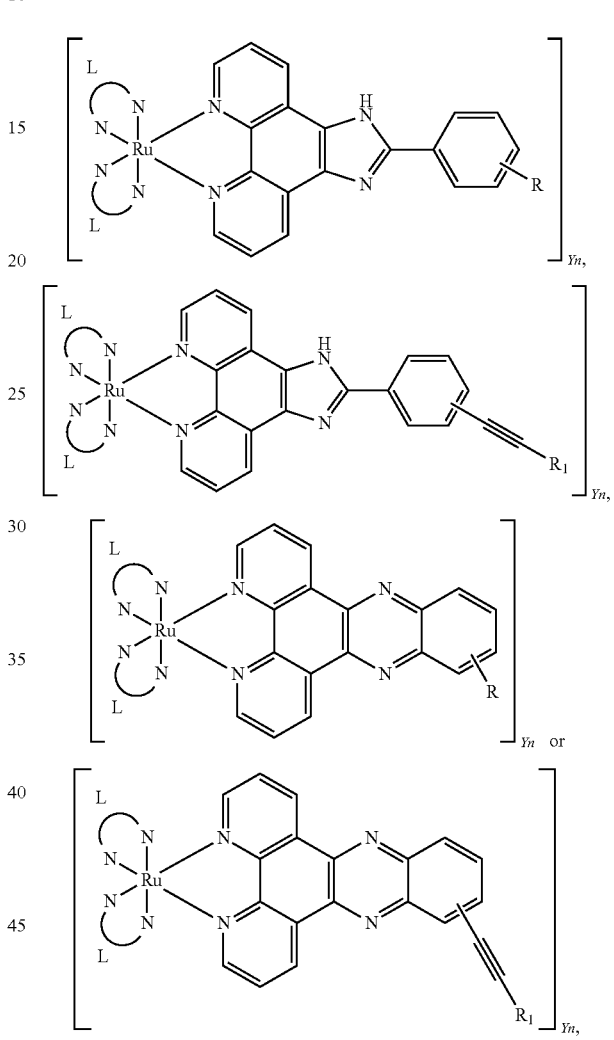

Wherein:

L is an auxiliary ligand having a structural formula of:

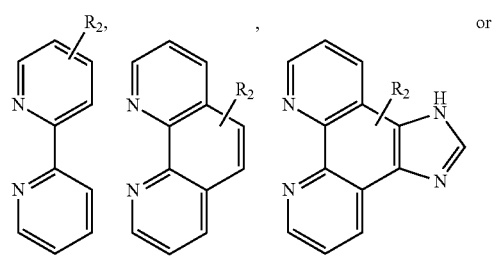

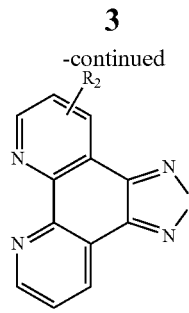

R is independently selected from substituted alkyl, substituted phenyl, substituted pyridyl, substituted furyl, substituted thiazole and substituted pyrrole, wherein substituted group is optionally selected from hydroxyl, nitro, halogen, amino, carboxyl, cyano, mercapto, $C_3$-$C_8$ cycloalkyl, $SO_3H$, $C_1$-$C_6$ alkyl, $C_2$-$C_6$ alkenyl, $C_2$-$C_6$ alkynyl, hydroxyl($C_1$-$C_6$)alkyl, amino($C_1$-$C_6$) alkyl, $CO_2R'$, $CONR'R'$, $COR'$, $SO_2R'R'$, ($C_1$-$C_6$) alkoxyl, ($C_1$-$C_6$)alkylsulphide, —N=NR', NR'R' or trifluoro($C_1$-$C_6$)alkyl; wherein R is selected from H, $C_1$-$C_6$ alkyl or phenyl; $R_1$ is independently selected from hydrogen, hydroxyl, trimethylsilyl, $C_1$-$C_6$ alkyl or substituted $C_1$-$C_6$ alkyl, phenyl or substituted phenyl, pyridyl or substituted pyridyl, furyl or substituted furyl, pyrryl or substituted pyrryl, thiazolyl or substituted thiazolyl; wherein the position of $R_1$ substituted ethynyl may be ortho-position, meta-position or para-position on the benzene ring; the number of substituted ethynyl is 1, 2 or more; $R_2$ is independently selected from methyl, methoxyl, nitro-group and halogen; Y is an ion or acidic radical ion which makes the whole ruthenium(II) complex electrically neutral, n is the number of ions or acidic radical ions which makes the whole ruthenium(II) complex electrically neutral;

The length of the nucleic acid sequence may be at least 4 base pairs (bp). In some embodiments, the length of the nucleic acid sequence may not be longer than 3,000 bp.

In one embodiment, the ruthenium complex may be a single chiral isomer thereof.

In some embodiments, the length of the nucleic acid sequence may not be longer than 3,000 bp. The nucleic acid is selected from the group consisting of c-myc promoter region DNA, C-kit promoter region DNA, bcl-2 promoter region DNA, miR-21, DNA of AS1411, SiRNA, microRNA, aptamer and mRNA.

In some embodiments, the nucleic acid may be a fluorophore-labeled nucleic acid.

In some embodiments, the invention also provides an application of a ruthenium coordination complex-nucleic acid complex used as a fluorescent probe, wherein the ruthenium complex is as previously described.

In some embodiments, the invention also provides a method of preparing ruthenium coordination complex-nucleic acid complex, comprising the following steps:

Uniformly mixing the ruthenium complex with the nucleic acid solution to obtain a mixture; then heating the mixture obtained to a temperature ranging from 70° C. to 100° C. and maintaining the temperature for a time period ranging from 30 seconds to 30 minutes;

Cooling the mixture; thereafter, removing free ruthenium complexes to form a ruthenium coordination complex-nucleic acid complex;

wherein the ruthenium complex has the following structural formula:

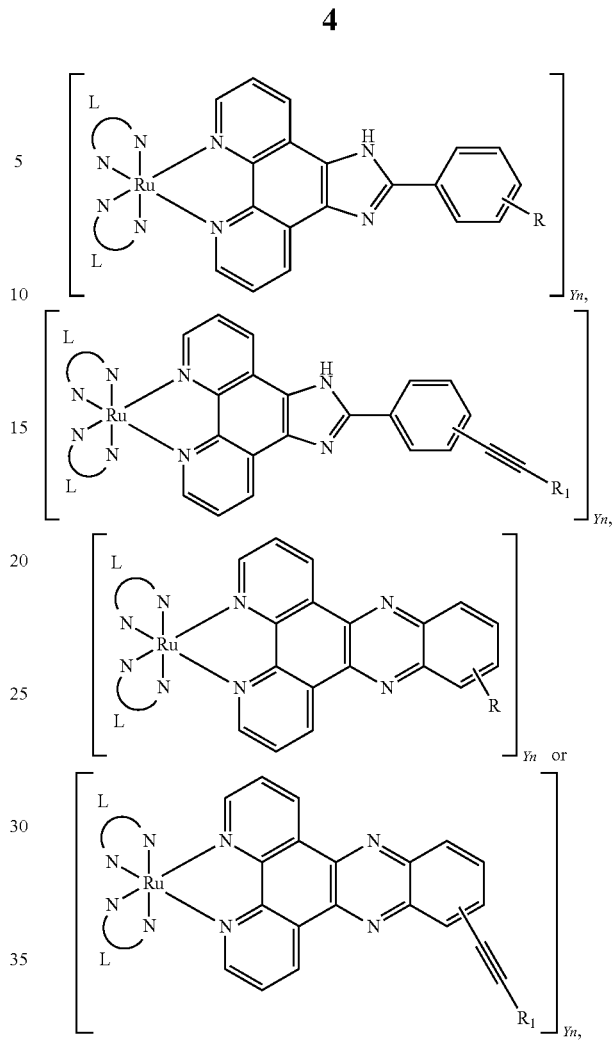

Wherein:
L is an auxiliary ligand having a structural formula of:

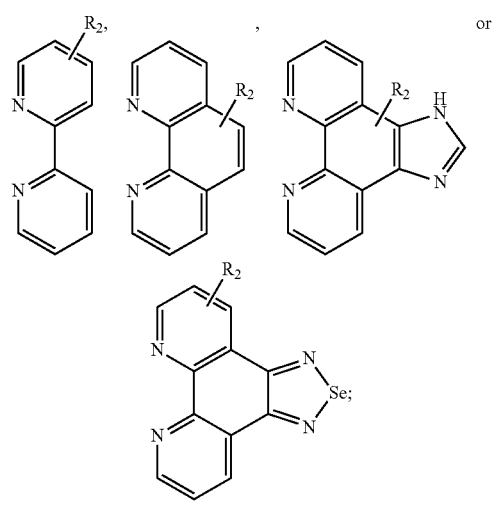

R is independently selected from substituted alkyl, substituted phenyl, substituted pyridyl, substituted furyl, substituted thiazole and substituted pyrrole, wherein substituted group is optionally selected from hydroxyl, nitro, halogen, amino, carboxy, cyano, mercapto, $C_3$-$C_8$ cycloalkyl, $SO_3H$, $C_1$-$C_6$ alkyl, $C_2$-$C_6$ alkenyl, $C_2$-$C_6$ alkynyl, hydroxyl($C_1$-$C_6$)alkyl, amino($C_1$-$C_6$)alkyl, CO₂R', CONR'R', COR', SO₂R'R', (C₁-C₆)alkoxyl, (C₁-C₆)alkylsulphide, —N=NR', NR'R' or trifluoro (C₁-C₆)alkyl; wherein R' is selected from H, C₁-C₆ alkyl or phenyl;

R₁ is independently selected from hydrogen, hydroxyl, trimethylsilyl, C₁-C₆ alkyl or substituted C₁-C₆ alkyl, phenyl or substituted phenyl, pyridyl or substituted pyridyl, furyl or substituted furyl, pyrryl or substituted pyrryl, thiazolyl or substituted thiazolyl; wherein the position of R₁ substituted ethynyl may be ortho-position, meta-position or para-position on the benzene ring; the number of substituted ethynyl is 1, 2 or more;

R₂ is independently selected from methyl, methoxyl, nitro and halogen;

Y is an ion or acidic radical ion which makes the whole ruthenium(II) complex be electrically neutral, n is the number of ions or acidic radical ions which makes the whole ruthenium(II) complex be electrically neutral;

In some embodiments, the ruthenium complex is selected from:

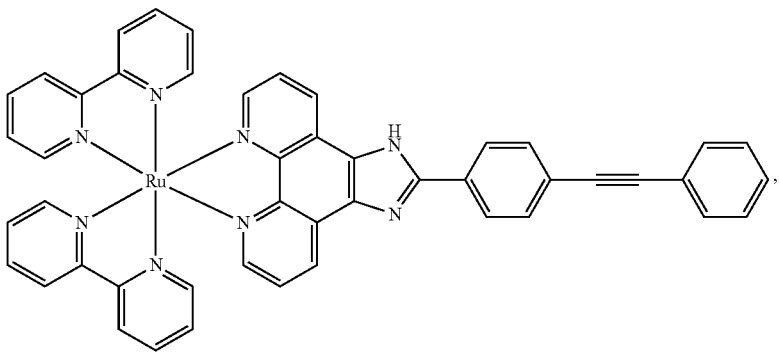

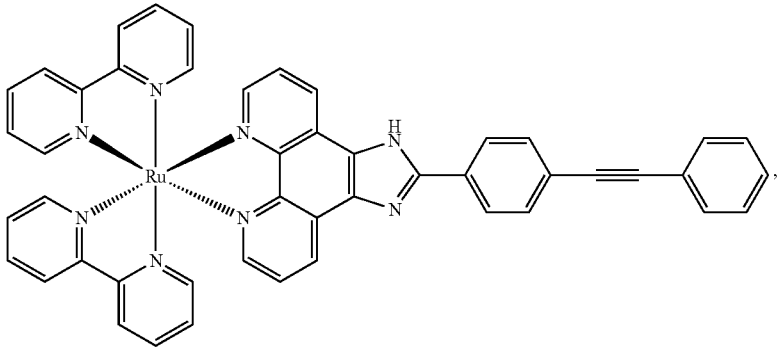

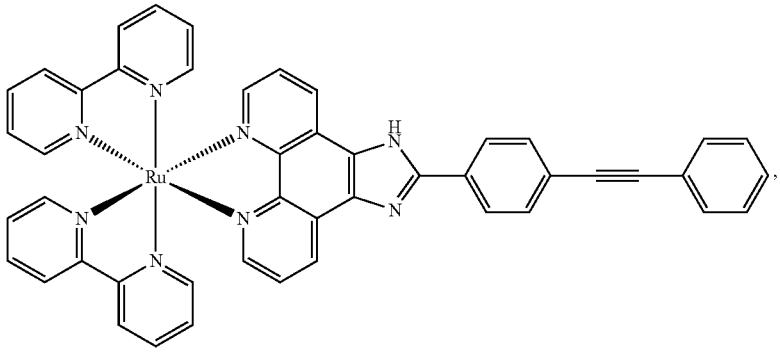

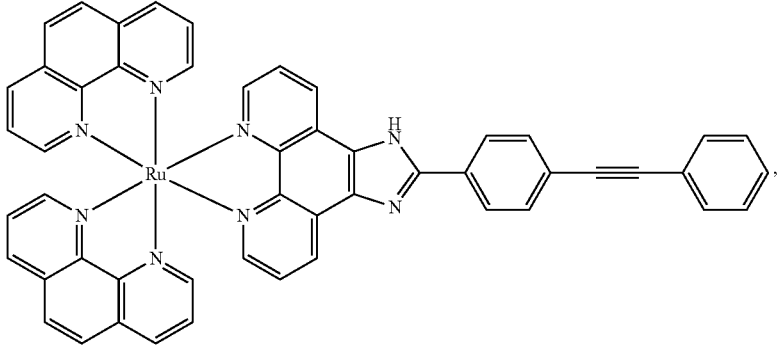

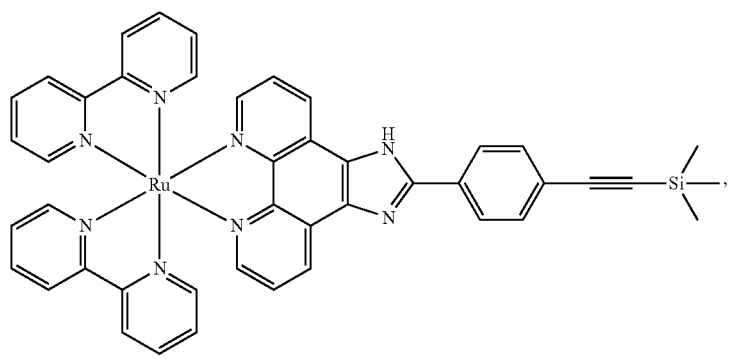
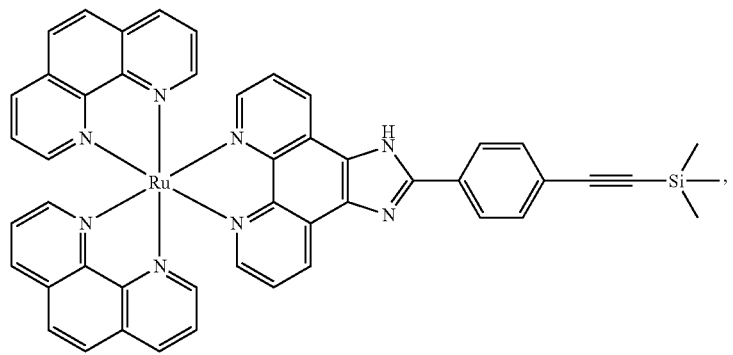
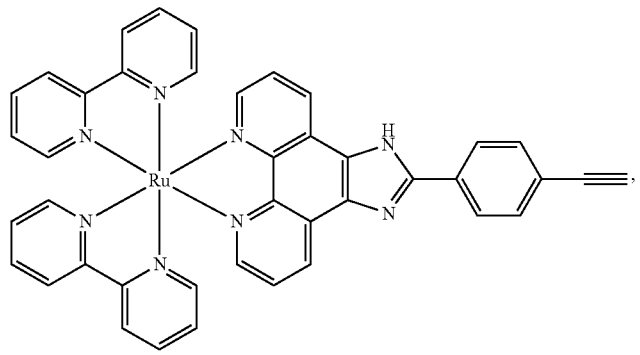
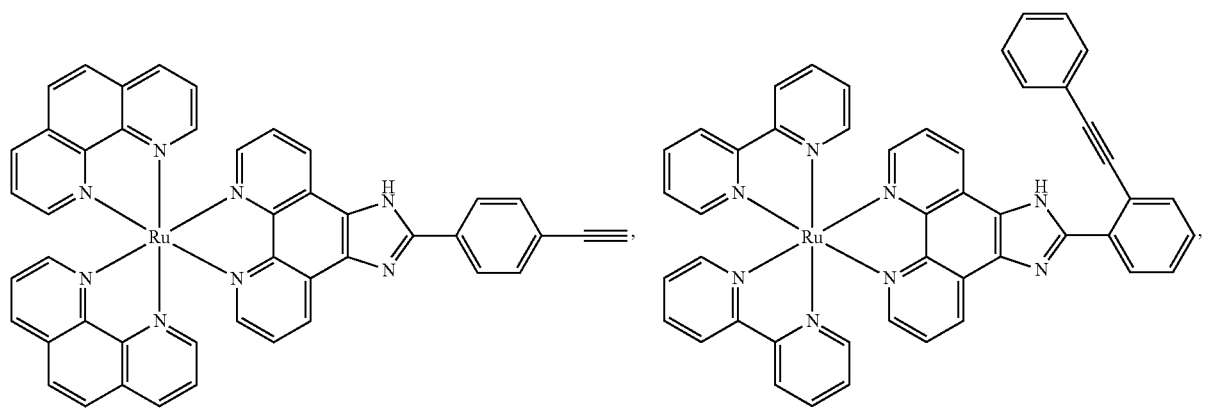

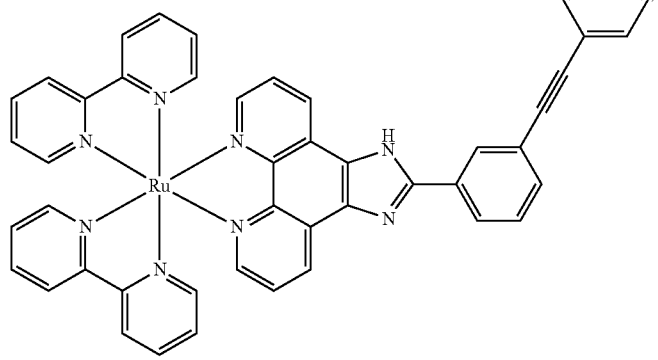
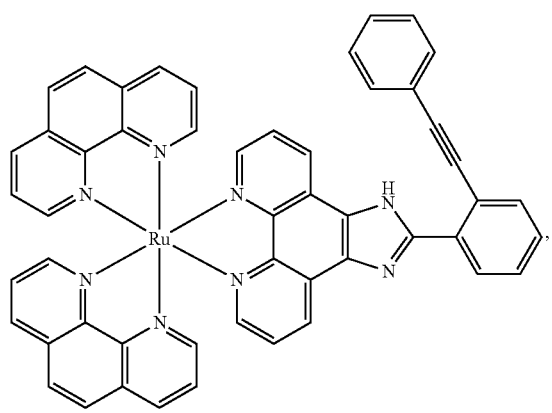
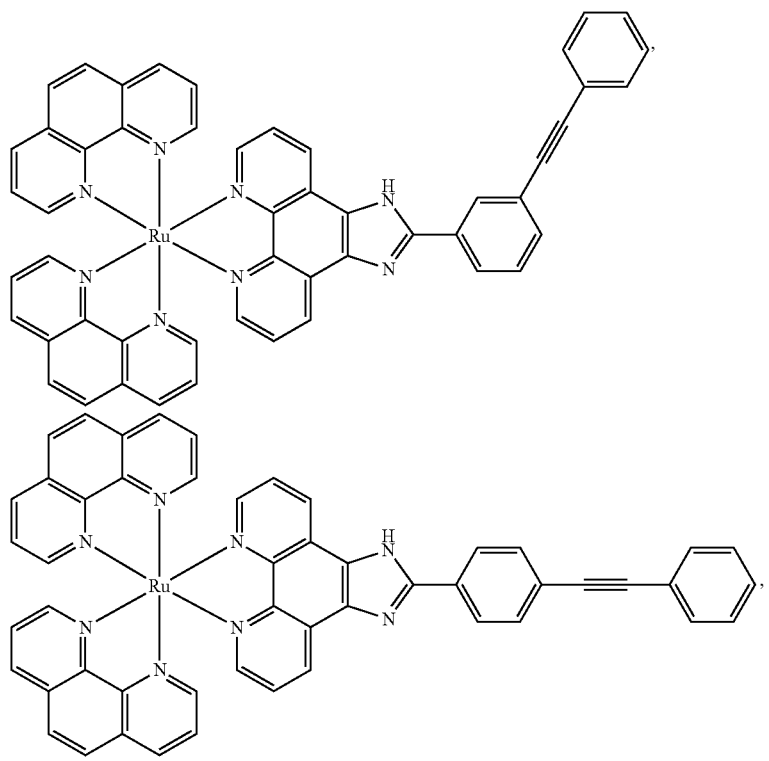

-continued
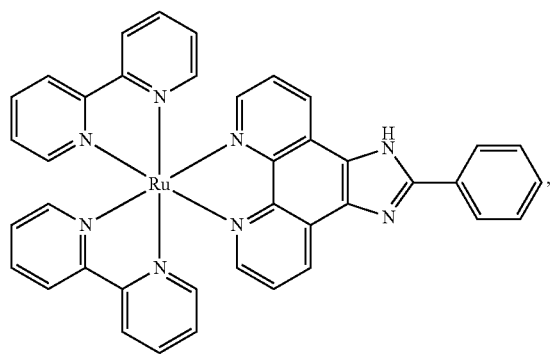
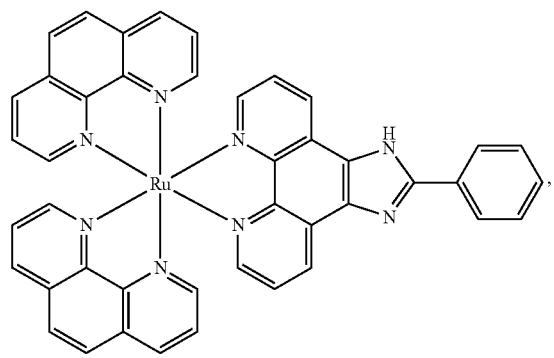
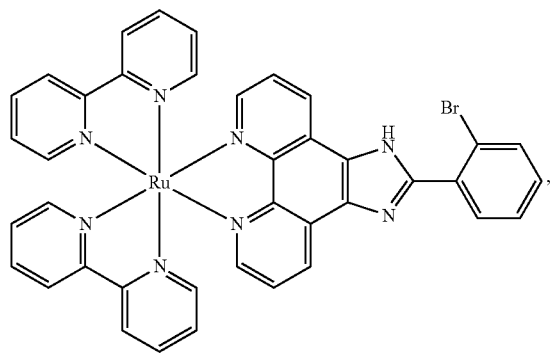
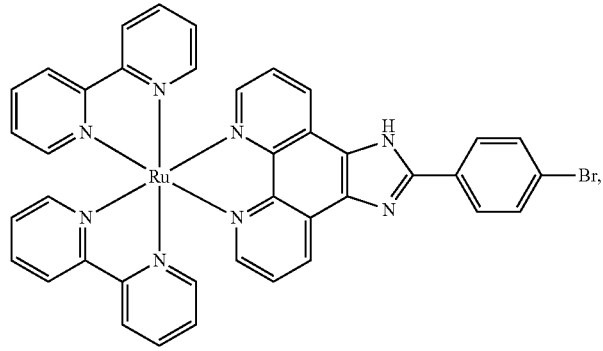
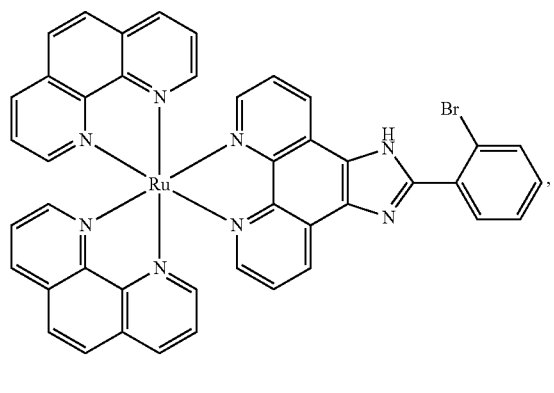
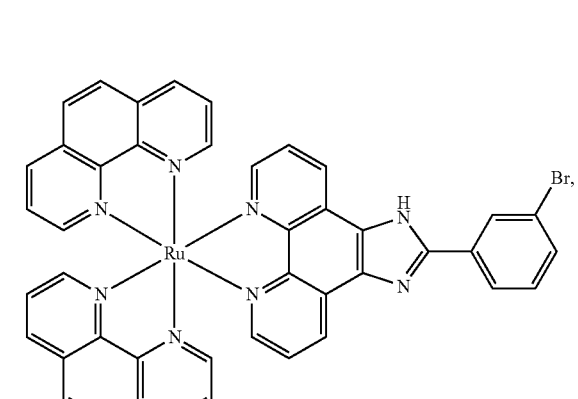
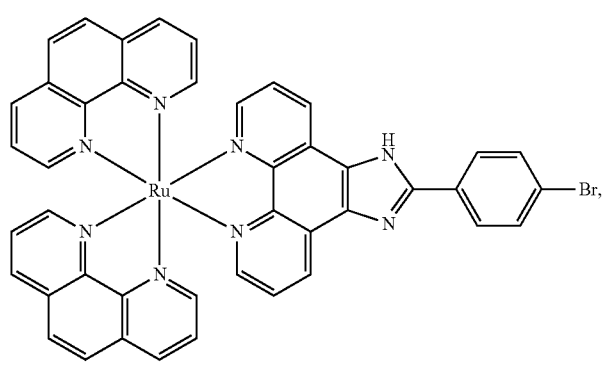
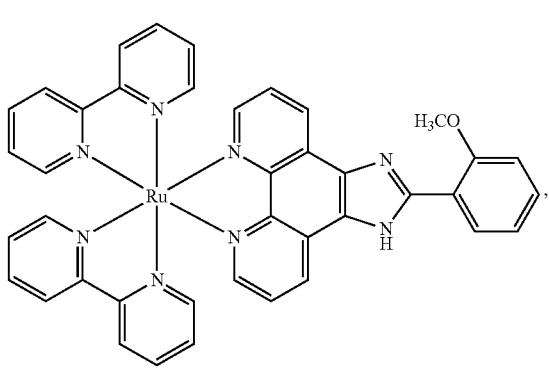

-continued
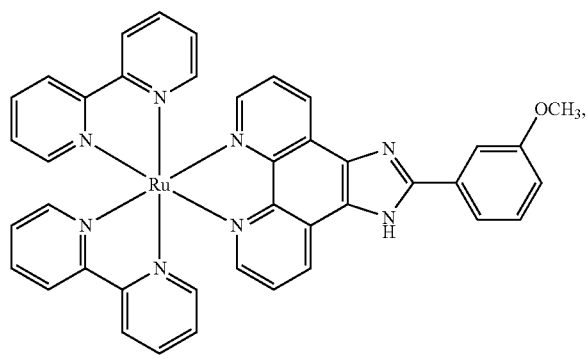
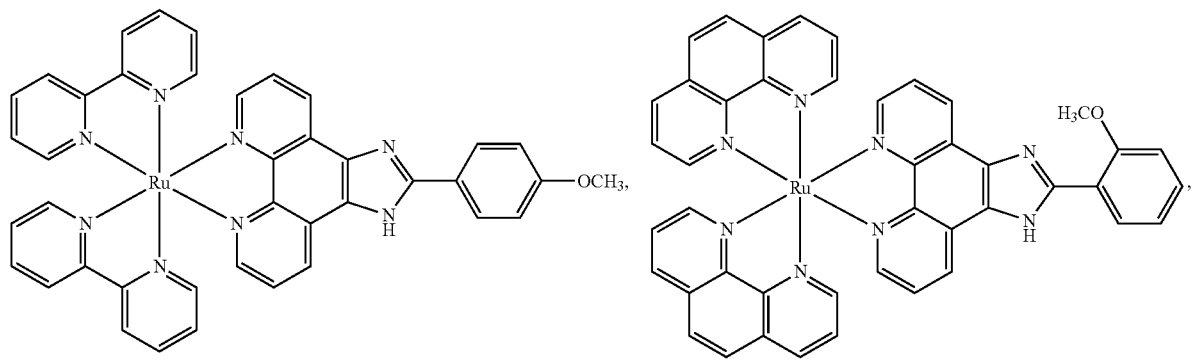
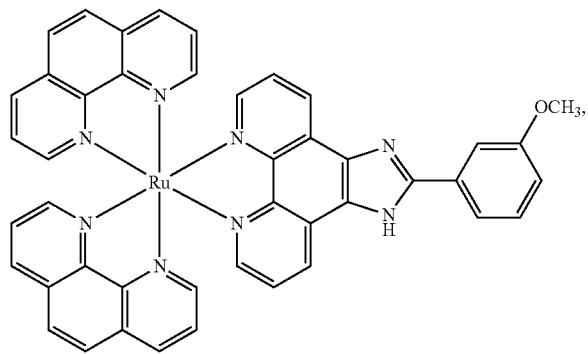
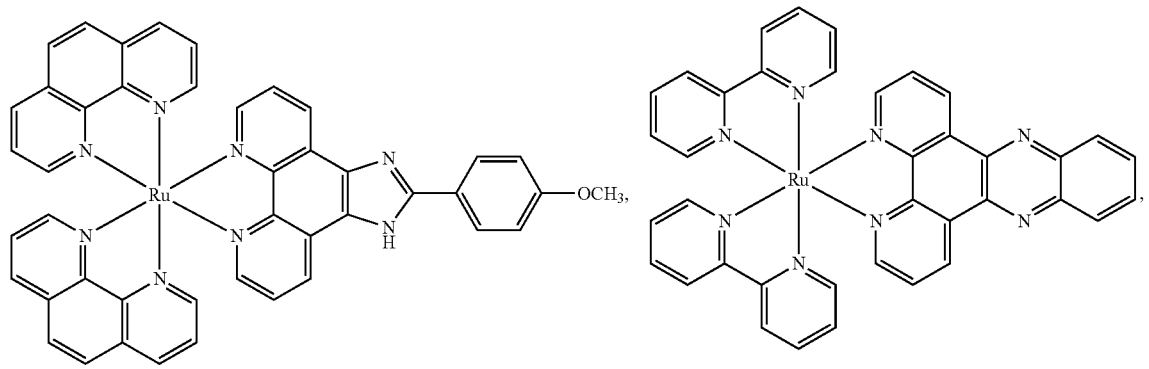

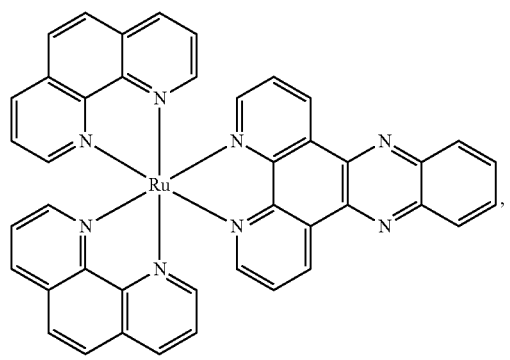

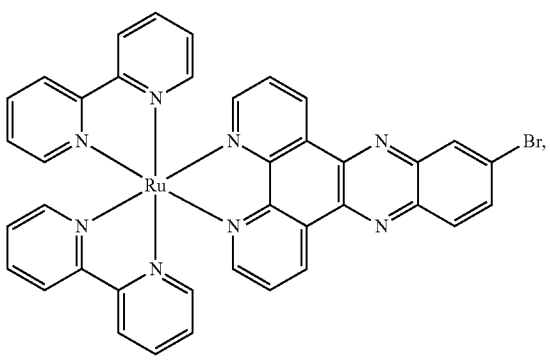

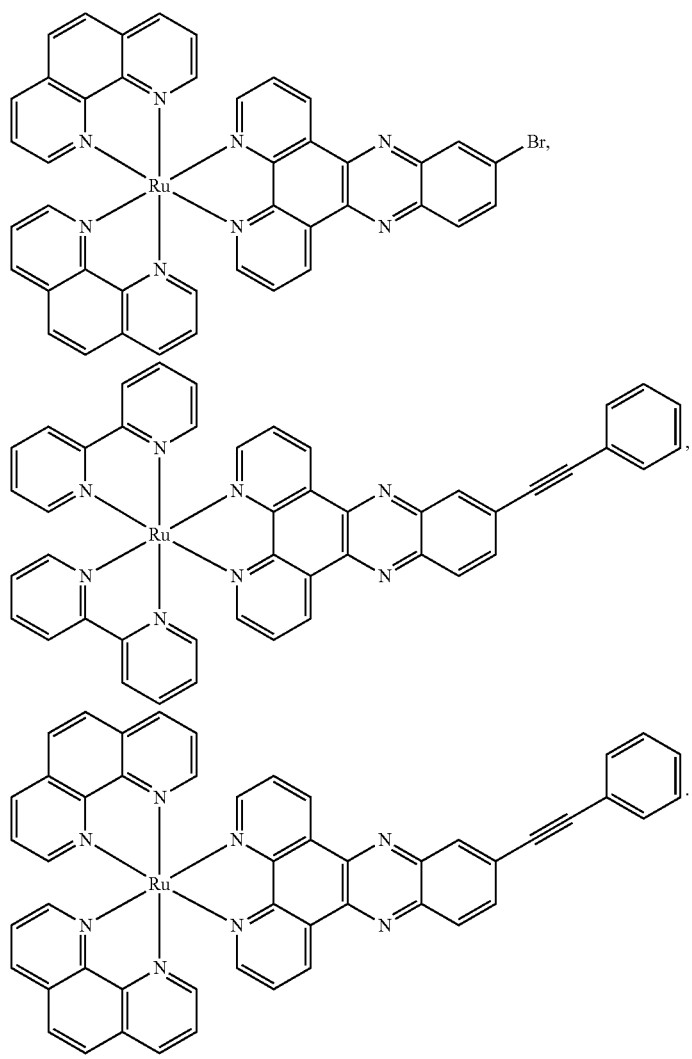

In some embodiments, the ruthenium complex is a single chiral isomer thereof.

In some embodiments, the length of the nucleic acid may not be shorter than 4 bp.

In one embodiment, the heating may be performed with a microwave.

In some embodiments, the nucleic acid may be a fluorophore-labeled nucleic acid.

The invention has the following advantageous effects:

The method for preparing a ruthenium coordination complex-nucleic acid complex in accordance with the present invention may provide a stable ruthenium coordination complex-nucleic acid complex in a more efficient manner and may provide many better effects.

DETAILED DESCRIPTION OF THE INVENTION

The ruthenium complexes used in the invention may be synthesized by methods of the applications (CN103709202A and CN103788134A) previously filed by the inventor or other known methods.

The technical schemes of the invention will be further described hereafter along with detailed examples.

The nucleic acid sequences used in the following examples are as follows:

```
c-myc Pu22:
                                    (SEQ ID NO: 1)
5'-TGAGGGTGGGGAGGGTGGGGAA-3'

Bcl-2 Pu27:
                                    (SEQ ID NO: 2)
5'-CGGGCGCGGGAGGAAGGGGCGGGAGC-3'
```

```
c-Kit 1:
                                    (SEQ ID NO: 3)
5'-GGGAGGGCGCTGGGAGGAGGG-3'

K-ras:
                                    (SEQ ID NO: 4)
5'-GCGGTGTGGGAAGAGGGAAGAGGGGGAGGCAG-3'

Telomere DNA sequence:
5'-TTAGGG-3'

AS1411 sequence:
                                    (SEQ ID NO: 5)
5'-GGTGGTGGTGGTTGTGGTGGTGGTGG-3' miR-21RNA sequence:
                                    (SEQ ID NO: 6)
5'-UAGCUUAUCAGACUGAUGUUGA-3'

PAR-1 siRNA:
                                    (SEQ ID NO: 7)
5'-AGAUUAGUCUCCAUCAUA-3'.
```

Figure 1:
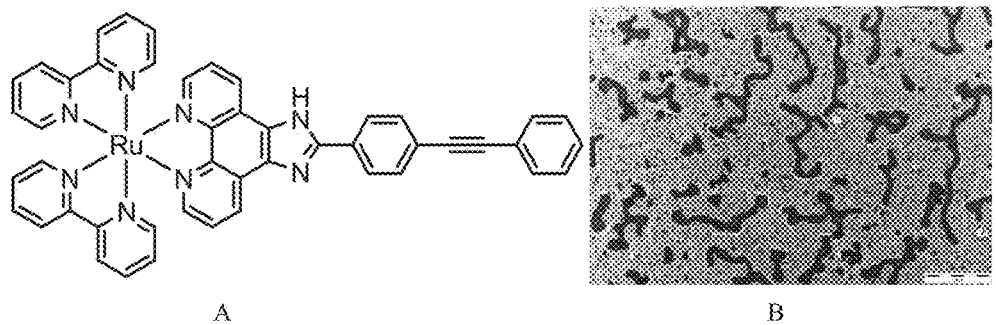
FIGS. 1-41 are structural formulas of the ruthenium coordination complexes used in examples 1-41 (if any) and Transmission Electron Microscopy images (TEMs) of the complexes obtained by combining the ruthenium coordination complexes with DNA respectively.

Example 1: Preparation of [Ru(bpy)$_2$pBEPIP](ClO$_4$)$_2$-c-myc Promoter Region DNA Complex Experimental method: 1 mM [Ru(bpy)2pBEPIP](ClO$_4$)$_2$ (FIG. 1A) is uniformly mixed with 1 mM c-myc Pu22 solution in a ratio of 1:1, then the mixture obtained is heated to 90° C. and maintained at that temperature for 30 seconds to 10 minutes, then the mixture is naturally cooled down to room temperature and left to stand for 24 hours at 4° C. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the c-myc Pu22 sequence to self-assemble into a nanotube structure (FIG. 1B).

Example 2: Preparation of [Ru(bpy)$_2$pBEPIP](ClO$_4$)$_2$-Telomere DNA Complex

Figure 2:
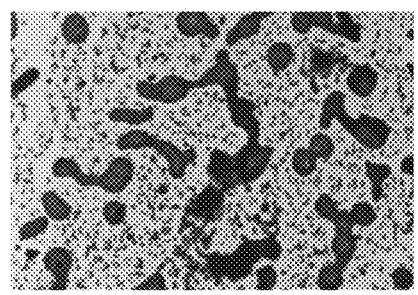

Experimental method: 1 mM [Ru(bpy)2pBEPIP](ClO$_4$)$_2$ is uniformly mixed with 1 mM DNA (5'-TTAGGG-3') solution in a ratio of 1:1, then the mixture obtained is heated to 90° C. and maintained at the temperature for 30 seconds to 10 minutes, then the mixture is naturally cooled down to room temperature and left to stand for 24 hours at 4° C. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into an analogous nanotube structure (FIG. 2).

Figure 3:
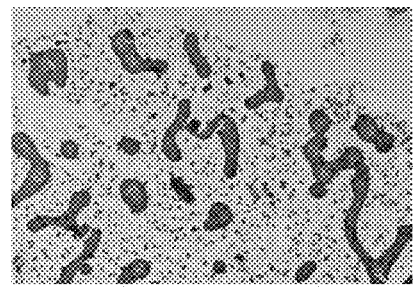

Example 3: Preparation of [Ru(bpy)$_2$pBEPIP](ClO$_4$)$_2$-bcl-2 Promoter Region DNA Complex Experimental method: 1 mM [Ru(bpy)$_2$pBEPIP](ClO$_4$)$_2$ is uniformly mixed with 1 mM Bcl-2 pu27 solution in a ratio of 1:1, then the mixture obtained is heated to 90° C. and maintained at the temperature for 30 seconds to 10 minutes, then the mixture is naturally cooled down to room temperature and left to stand for 24 hours at 4° C. The reaction mixture is dialyzed against distilled water to remove the polypyridyl ruthenium (II) complexes unloaded onto the nucleic acid, thereby forming a polypyridyl ruthenium (II)

coordination complex-nucleic acid complex. TEM revealed that the ruthenium complex facilitates the telomere DNA sequence to self-assemble into an analogous nanotube structure (FIG. 3).

Figure 4:
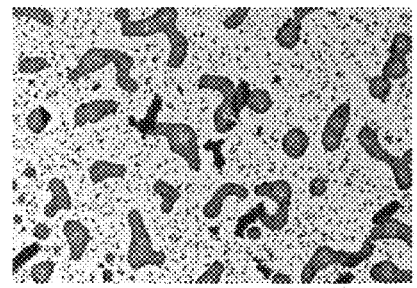

Example 4: Preparation of [Ru(Bpy)$_2$pBEPIP](ClO$_4$)$_2$-c-Kit Promoter Region DNA Nano-Complex Experimental method: 1 mM [Ru(bpy)$_2$pBEPIP](ClO$_4$)$_2$ is uniformly mixed with 1 mM c-kit pu27 solution in a ratio of 1:1, then the mixture obtained is heated to 90° C. under microwave radiation and maintained at the temperature for 30 seconds to 10 minutes, then the mixture is naturally cooled down to room temperature. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into an analogous nanotube structure (FIG. 4).

Figure 5:
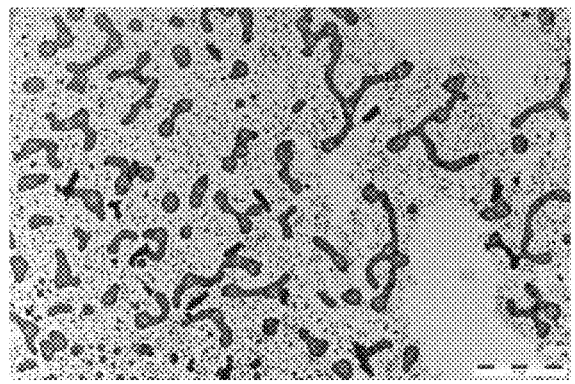

Example 5: Preparation of [Ru(bpy)$_2$pBEPIP](ClO$_4$)$_2$-K-Ras Promoter Region DNA Nano-complex Experimental method: 1 mM [Ru(bpy)$_2$pBEPIP](ClO$_4$)$_2$ is uniformly mixed with 1 mM K-Ras pu32 solution in a ratio of 1:1, then the mixture obtained is heated to 90° C. under microwave radiation and maintained at the temperature for 30 seconds to 10 minutes, then the mixture is naturally cooled down to room temperature. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into an analogous nanotube structure (FIG. 5).

Figure 6:
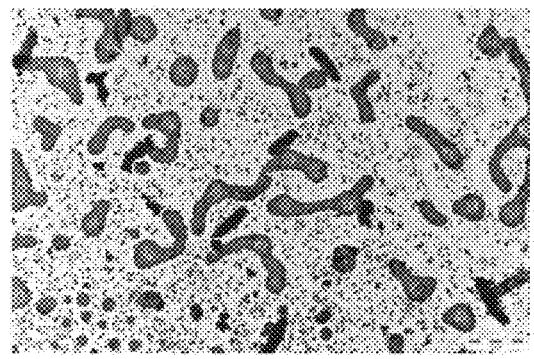

Example 6: Preparation of [Ru(bpy)$_2$pBEPIP]Cl$_2$-Aptamer AS1411 DNA Nano-complex Experimental method: 1 mM [Ru(bpy)$_2$pBEPIP]Cl$_2$ is uniformly mixed with 1 mM AS1411 DNA solution in a ratio of 1:1, then the mixture obtained is heated to 90° C. under microwave radiation and maintained at the temperature for 30 seconds to 10 minutes, then the mixture is naturally cooled down to room temperature. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into an analogous nanotube structure (FIG. 6).

Example 7: Preparation of [Ru(bpy)$_2$pBEPIP]Cl$_2$-CT-DNA Nano-Complex

Figure 7:
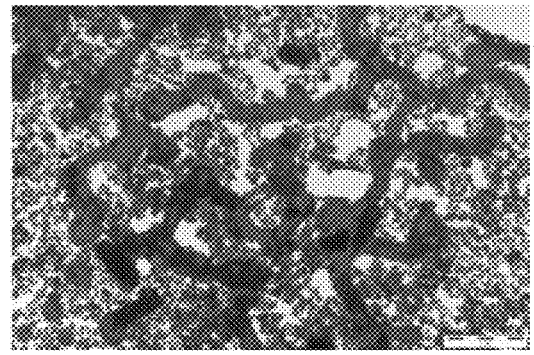

Experimental method: 1 mM [Ru(bpy)$_2$pBEPIP]Cl$_2$ is uniformly mixed with 1 mM CT-DNA solution in a ratio of 1:1, then the mixture obtained is heated to 90° C. under microwave radiation and maintained at the temperature for 30 seconds to 10 minutes, then the mixture is naturally cooled down to room temperature and left to stand for 24 hours at 4° C. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into an analogous nanotube structure (FIG. 7).

Figure 8:
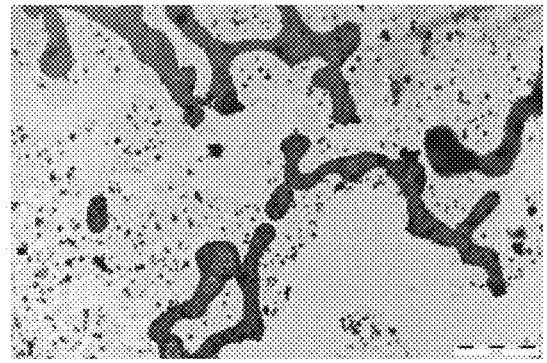

Example 8: Preparation of [Ru(bpy)$_2$pBEPIP](ClO$_4$)$_2$-miR-21 Nano-Complex Experimental method: 1 mM [Ru(bpy)$_2$pBEPIP](ClO$_4$)$_2$ is uniformly mixed with 10 mM miR-21 solution in a ratio of 1:1, then the mixture obtained is heated to 90° C. under microwave radiation and maintained at the temperature for 30 seconds to 10 minutes, then the mixture is naturally cooled down to room temperature and left to stand for 24 hours at 4° C. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into analogous nanotube structure (FIG. 8).

Figure 9:
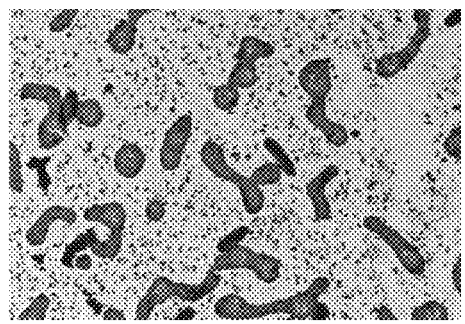

Example 9: Preparation of [Ru(bpy)$_2$pBEPIP](ClO$_4$)$_2$-PAR-1 SiRNA Nano-Complex Experimental method: 10 mM [Ru(bpy)$_2$pBEPIP](ClO$_4$)$_2$ is uniformly mixed with 1 mM SiRNA solution in a ratio of 10:1, then the mixture obtained is heated to 90° C. under microwave radiation and maintained at the temperature for 30 seconds to 10 minutes, then the mixture is naturally cooled down to room temperature and left to stand for 24 hours at 4° C. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into an analogous nanotube structure (FIG. 9).

Figure 10:
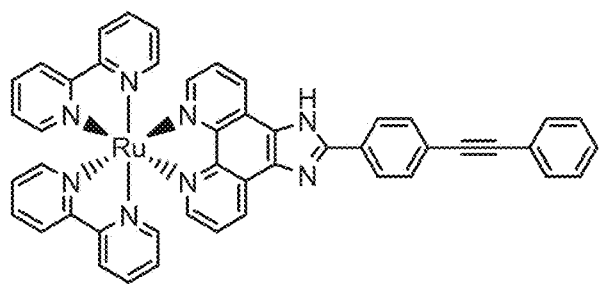
Figure 10:
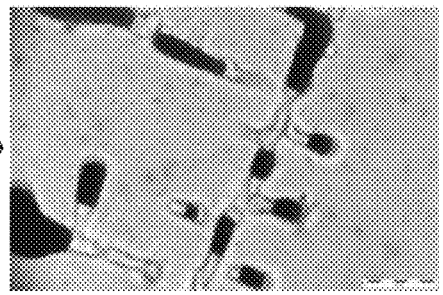

Example 10: Preparation of Λ-[Ru(bpy)$_2$pBEPIP](ClO$_4$)$_2$-c-myc pu22 DNA Nano-Complex Experimental method: 1 mM Λ-[Ru(bpy)$_2$pBEPIP](ClO$_4$)$_2$ (FIG. 10A) is uniformly mixed with 1 mM c-myc Pu22 DNA solution in a ratio of 1:1, then the mixture obtained is heated to 90° C. and maintained at the temperature for 30 seconds to 10 minutes, then the mixture is naturally cooled down to room temperature and left to stand for 24 hours at 4° C. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into an analogous nanotube structure (FIG. 10B).

Figure 11:
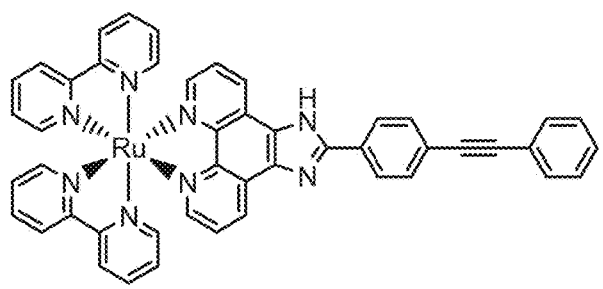
Figure 11:
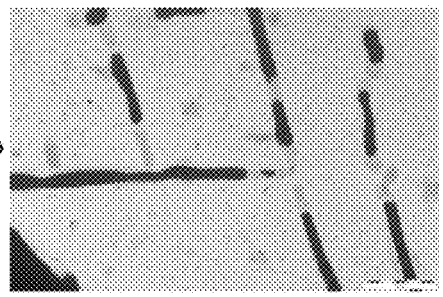

Example 11: Preparation of Δ-[Ru(bpy)$_2$pBEPIP](ClO$_4$)$_2$-c-myc Promoter Region DNA Nano-Complex Experimental method: 1 mM Δ-[Ru(bpy)$_2$pBEPIP](ClO$_4$)$_2$ (FIG. 11A) is uniformly mixed with 1 mM c-myc Pu22 DNA solution in a ratio of 1:1, then the mixture obtained is heated to 90° C. and maintained at the temperature for 30 seconds to 10 minutes, then the mixture is naturally cooled down to room temperature and left to stand for 24 hours at 4° C. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into an analogous nanotube structure (FIG. 11B).

Figure 12:
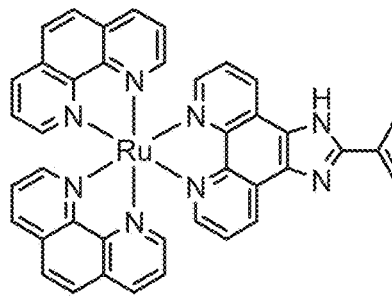
Figure 12:
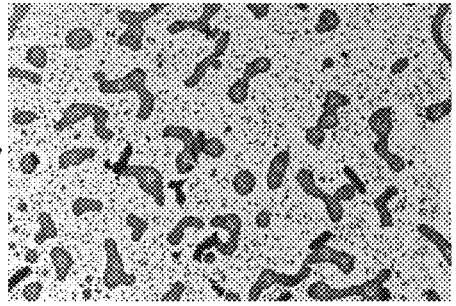

Example 12: Preparation of [Ru(phen)$_2$pBEPIP] (ClO$_4$)$_2$-c-myc Promoter Region DNA Nano-Complex Experimental method: 1 mM [Ru(phen)$_2$pBEPIP](ClO$_4$)$_2$ (FIG. 12A) is uniformly mixed with 1 mM c-myc Pu22 DNA solution in a ratio of 1:1, then the mixture obtained is heated to 90° C. and maintained at the temperature for 30 seconds to 10 minutes, then the mixture is naturally cooled down to room temperature and left to stand for 24 hours at 4° C. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into an analogous nanotube structure (FIG. 12B).

Figure 13:
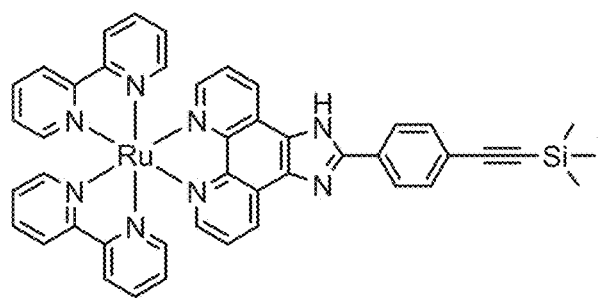
Figure 13:
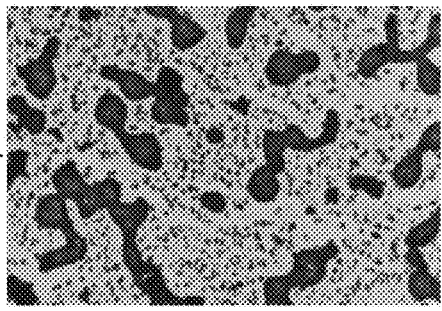

Example 13: Preparation of [Ru(bpy)$_2$pTEPIP] (ClO$_4$)$_2$-c-myc Promoter Region DNA Nano-Complex Experimental method: 1 mM [Ru(bpy)$_2$pTEPIP](ClO$_4$)$_2$ (FIG. 13A) is uniformly mixed with 1 mM c-myc Pu22 DNA solution in a ratio of 1:1, then the mixture obtained is heated to 90° C. under microwave radiation and maintained at the temperature for 30 seconds to 10 minutes, then the mixture is naturally cooled down to room temperature and left to stand for 24 hours at 4° C. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into an analogous nanotube structure (FIG. 13B).

Figure 14:
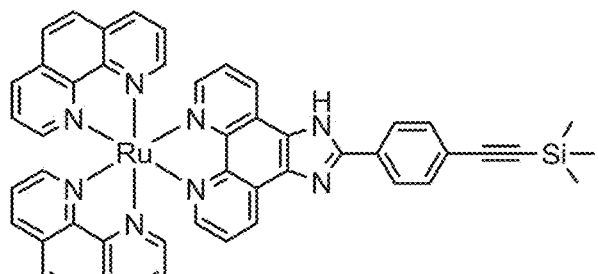
Figure 14:
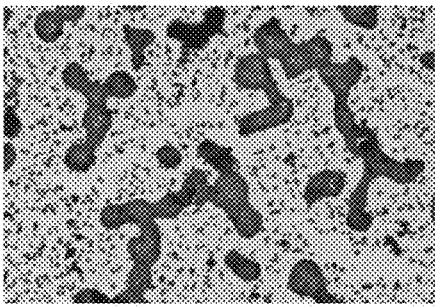

Example 14: Preparation of [Ru(phen)$_2$pTEPIP] (ClO$_4$)$_2$-c-myc Promoter Region DNA Nano-Complex Experimental method: 1 mM [Ru(phen)$_2$pTEPIP](ClO$_4$)$_2$ (FIG. 14A) is uniformly mixed with 1 mM c-myc Pu22 DNA solution in a ratio of 1:1, then the mixture obtained is heated to 90° C. under microwave radiation and maintained at the temperature for 30 seconds to 10 minutes, then the mixture is naturally cooled down to room temperature and left to stand for 24 hours at 4° C. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into an analogous nanotube structure (FIG. 14B).

Figure 15:
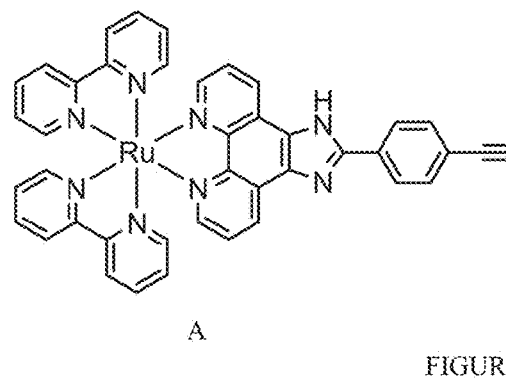
Figure 15:
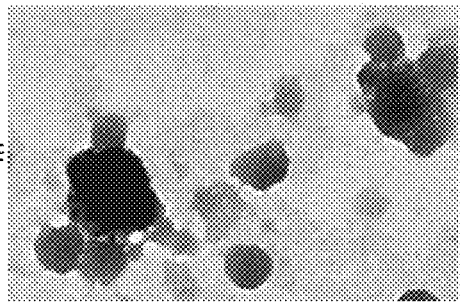

Example 15: Preparation of [Ru(bpy)$_2$pEPIP] (ClO$_4$)$_2$-c-myc Promoter Region DNA Nano-Complex Experimental method: 1 mM [Ru(bpy)$_2$pEPIP](ClO$_4$)$_2$ (FIG. 15A) is uniformly mixed with 1 mM c-myc Pu22 DNA solution in a ratio of 1:1, then the mixture obtained is heated to 90° C. under microwave radiation and maintained at the temperature for 30 seconds to 10 minutes, then the mixture is naturally cooled down to room temperature and left to stand for 24 hours at 4° C. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into an analogous nanotube structure (FIG. 15B).

Figure 16:
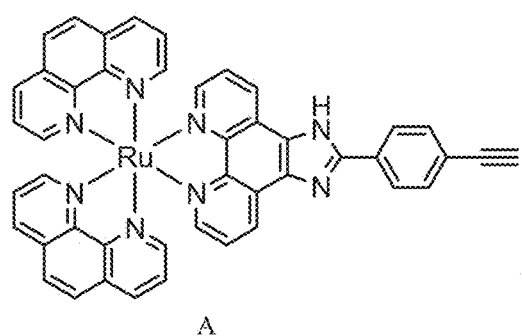
Figure 16:
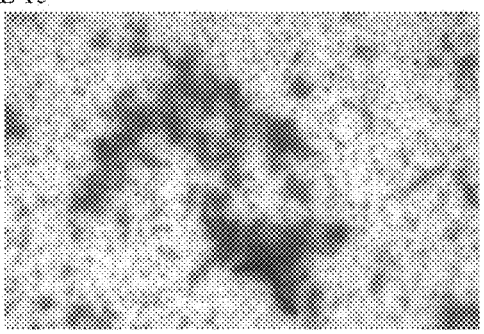

Example 16: Preparation of [Ru(phen)$_2$pEPIP] (ClO$_4$)$_2$-c-myc Promoter Region DNA Nano-Complex Experimental method: 1 mM [Ru(phen)$_2$pEPIP](ClO$_4$)$_2$ (FIG. 16A) is uniformly mixed with 1 mM c-myc Pu22 DNA solution in a ratio of 1:1, then the mixture obtained is heated to 90° C. under microwave radiation and maintained at the temperature for 30 seconds to 10 minutes, then the mixture is naturally cooled down to room temperature and left to stand for 24 hours at 4° C. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into an analogous nanotube structure (FIG. 16B).

Figure 17:
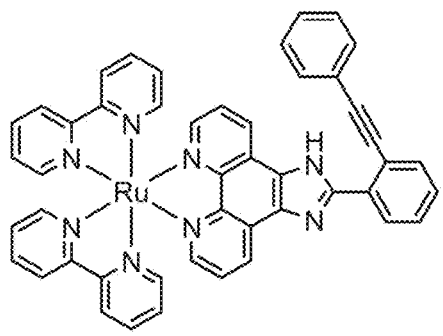
Figure 17:
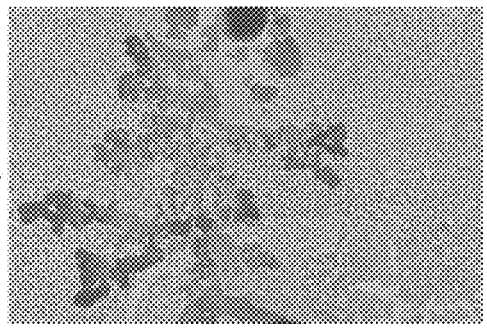

Example 17: Preparation of [Ru(bpy)$_2$oBEPIP] (ClO$_4$)$_2$-c-myc Promoter Region DNA Nano-Complex Experimental method: 1 mM [Ru(bpy)$_2$oBEPIP](ClO$_4$)$_2$ (FIG. 17A) is uniformly mixed with 1 mM c-myc Pu22 DNA solution in a ratio of 1:1, then the mixture obtained is heated to 90° C. under microwave radiation and maintained at the temperature for 30 seconds to 10 minutes, then the mixture is naturally cooled down to room temperature and left to stand for 24 hours at 4° C. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into an analogous nanotube structure (FIG. 17B).

Figure 18:
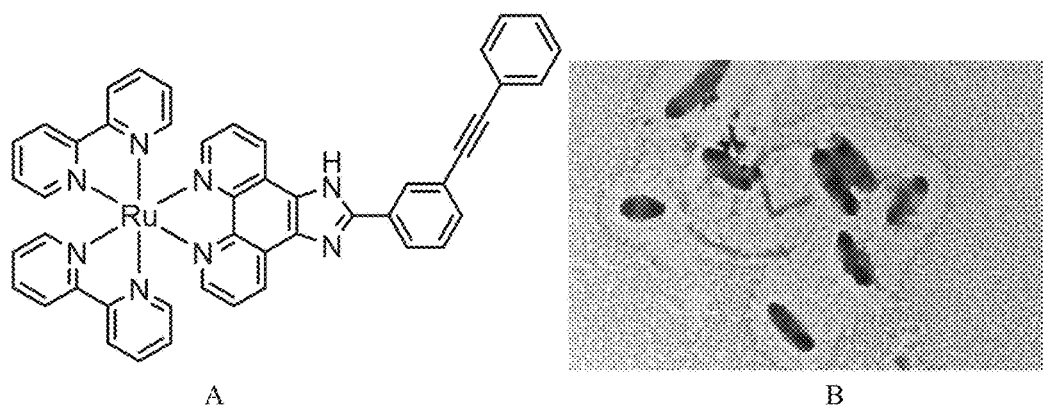

Example 18: Preparation of [Ru(bpy)$_2$mBEPIP] (ClO$_4$)$_2$-c-myc Promoter Region DNA Nano-Complex Experimental method: 1 mM [Ru(bpy)$_2$mBEPIP](ClO$_4$)$_2$ (FIG. 18A) is uniformly mixed with 1 mM c-myc Pu22 DNA solution in a ratio of 1:1, then the mixture obtained is heated to 90° C. under microwave radiation and maintained at the temperature for 30 seconds to 10 minutes, then the mixture is naturally cooled down to room temperature and left to stand for 24 hours at 4° C. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into an analogous nanotube structure (FIG. 18B).

Figure 19:
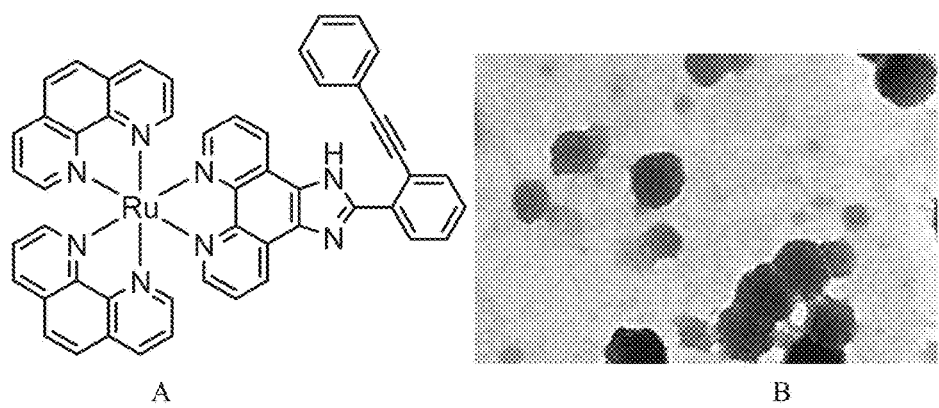

Example 19: Preparation of [Ru(phen)$_2$oBEPIP](ClO$_4$)$_2$-c-myc Promoter Region DNA Nano-Complex Experimental method: 1 mM [Ru(phen)$_2$oBEPIP](ClO$_4$)$_2$ (FIG. 19A) is uniformly mixed with 1 mM c-myc Pu22 DNA solution in a ratio of 1:1, then the mixture obtained is heated to 90° C. under microwave radiation and maintained at the temperature for 30 seconds to 10 minutes, then the mixture is naturally cooled down to room temperature and left to stand for 24 hours at 4° C. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into an analogous nanotube structure (FIG. 19B).

Figure 20:
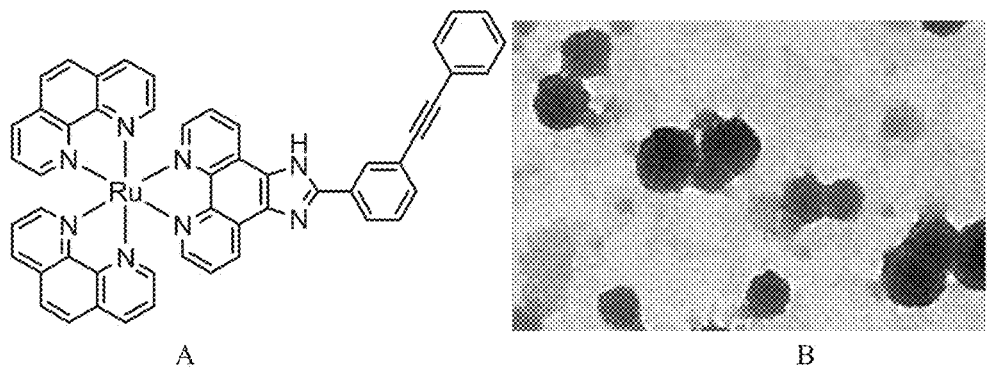

Example 20: Preparation of [Ru(phen)$_2$mBEPIP](ClO$_4$)$_2$-c-myc Promoter Region DNA Nano-Complex Experimental method: 1 mM [Ru(phen)$_2$mBEPIP](ClO$_4$)$_2$ (FIG. 20A) is uniformly mixed with 1 mM c-myc Pu22 DNA solution in a ratio of 1:1, then the mixture obtained is heated to 90° C. under microwave radiation and maintained at the temperature for 30 seconds to 10 minutes, then the mixture is naturally cooled down to room temperature and left to stand for 24 hours at 4° C. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into an analogous nanotube structure (FIG. 20B).

Figure 21:
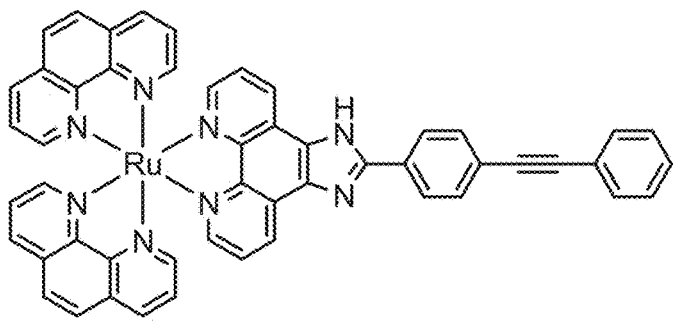
Figure 21:
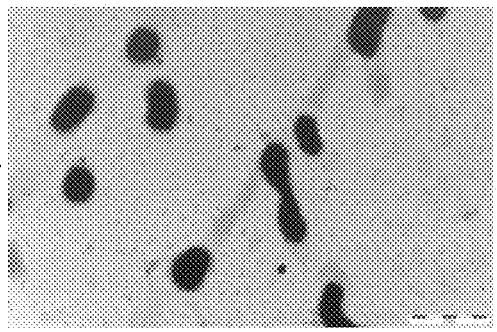

Example 21: Preparation of [Ru(phen)$_2$pBEPIP](ClO$_4$)$_2$-c-myc Promoter Region DNA Nano-Complex Experimental method: 1 mM [Ru(phen)$_2$pBEPIP](ClO$_4$)$_2$ (FIG. 21A) is uniformly mixed with 1 mM c-myc Pu22 DNA solution in a ratio of 1:1, then the mixture obtained is heated to 90° C. under microwave radiation and maintained at the temperature for 30 seconds to 10 minutes, then the mixture is naturally cooled down to room temperature and left to stand for 24 hours at 4° C. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into an analogous nanotube structure (FIG. 21B).

Figure 22:
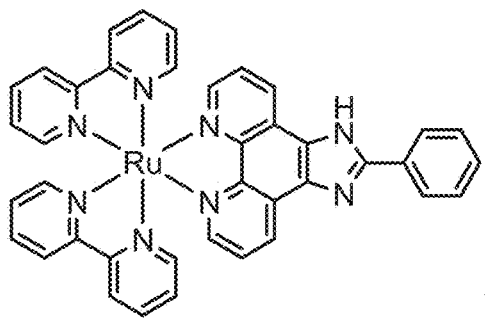
Figure 22:
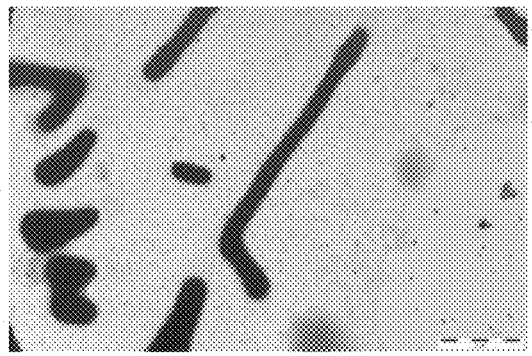

Example 22: Preparation of [Ru(bpy)$_2$PIP](ClO$_4$)$_2$-c-myc Promoter Region DNA Nano-Complex Experimental method: 10 mM [Ru(bpy)$_2$PIP](ClO$_4$)$_2$ (FIG. 22A) is uniformly mixed with 1 mM c-myc Pu22 DNA solution in a ratio of 10:1, then the mixture obtained is heated to 90° C. under microwave radiation and maintained at the temperature for 30 seconds to 10 minutes, then the mixture is naturally cooled down to room temperature and left to stand for 24 hours at 4° C. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into an analogous nanotube structure (FIG. 22B).

Figure 23:
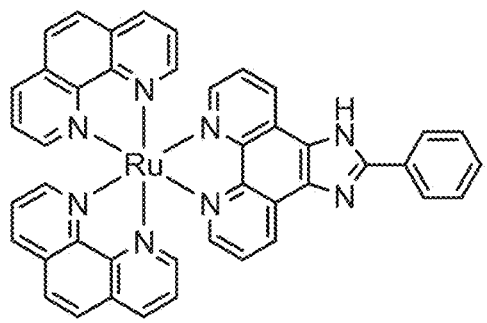
Figure 23:
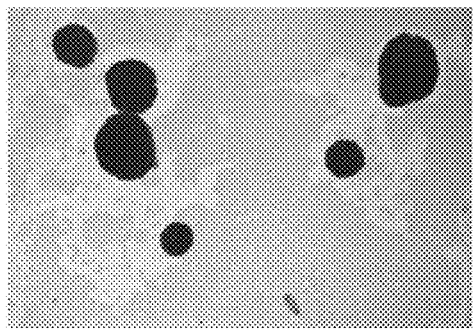

Example 23: Preparation of [Ru(phen)$_2$PIP](ClO$_4$)$_2$-c-myc Promoter Region DNA Nano-Complex Experimental method: 10 mM [Ru(phen)$_2$PIP](ClO$_4$)$_2$ (FIG. 23A) is uniformly mixed with 1 mM c-myc Pu22 DNA solution in a ratio of 10:1, then the mixture obtained is heated to 90° C. under microwave radiation and maintained at the temperature for 30 seconds to 10 minutes, then the mixture is naturally cooled down to room temperature and left to stand for 24 hours at 4° C. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into an analogous nanotube structure (FIG. 23B).

Figure 24:
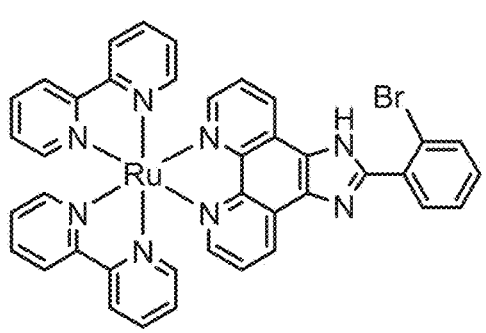
Figure 24:
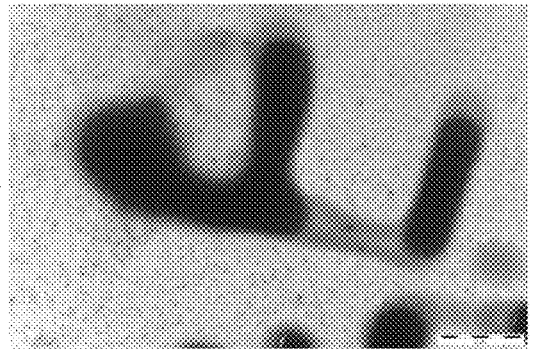

Example 24: Preparation of [Ru(bpy)$_2$oBrPIP](ClO$_4$)$_2$-c-myc Promoter Region DNA Nano-Complex Experimental method: 1 mM [Ru(bpy)$_2$oBrPIP](ClO$_4$)$_2$ (FIG. 24A) is uniformly mixed with 10 mM c-myc Pu22 DNA solution in a ratio of 1:10, then the mixture obtained is heated to 90° C. under microwave radiation and maintained at the temperature for 30 seconds to 10 minutes, then the mixture is naturally cooled down to room temperature. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into an analogous nanotube structure (FIG. 24B).

Figure 25:
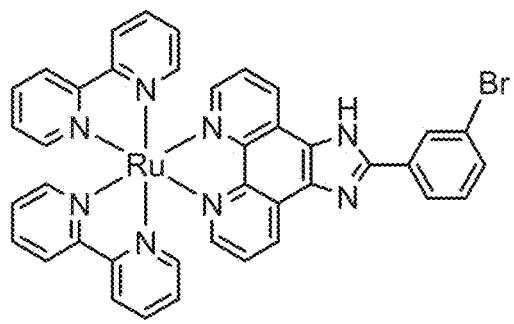
Figure 25:
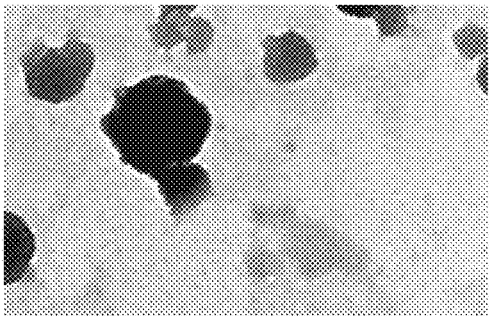

Example 25: Preparation of [Ru(bpy)$_2$mBrPIP](ClO$_4$)$_2$-c-myc Promoter Region DNA Nano-Complex Experimental method: 1 mM [Ru(bpy)$_2$mBrPIP](ClO$_4$)$_2$ (FIG. 25A) is uniformly mixed with 10 mM c-myc Pu22 DNA solution in a ratio of 1:10, then the mixture obtained is heated to 90° C. under microwave radiation and maintained at the temperature for 30 seconds to 10 minutes, then the mixture is naturally cooled down to room temperature. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into an analogous nanotube structure (FIG. 25B).

Figure 26:
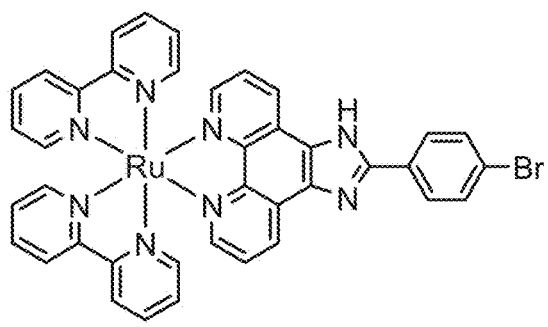
Figure 26:
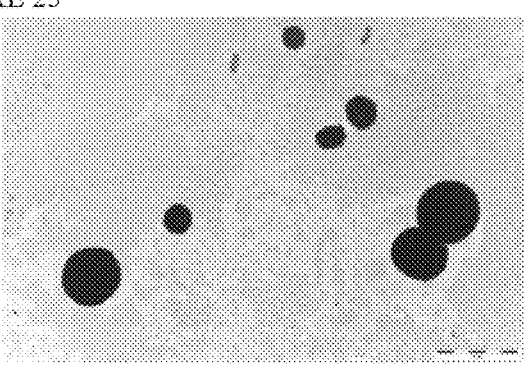

Example 26: Preparation of [Ru(bpy)$_2$pBrPIP] (ClO$_4$)$_2$-c-myc Promoter Region DNA Nano-Complex Experimental method: 1 mM [Ru(bpy)$_2$pBrPIP](ClO$_4$)$_2$ (FIG. 26A) is uniformly mixed with 1 mM c-myc Pu22 DNA solution in a ratio of 1:1, then the mixture obtained is heated to 90° C. under microwave radiation and maintained at the temperature for 30 seconds to 10 minutes, then the mixture is naturally cooled down to room temperature and left to stand for 24 hours at 4° C. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into an analogous nanotube structure (FIG. 26B).

Figure 27:
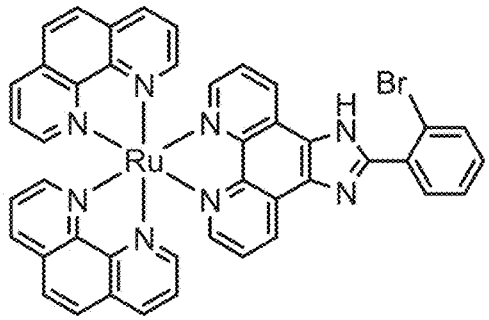
Figure 27:
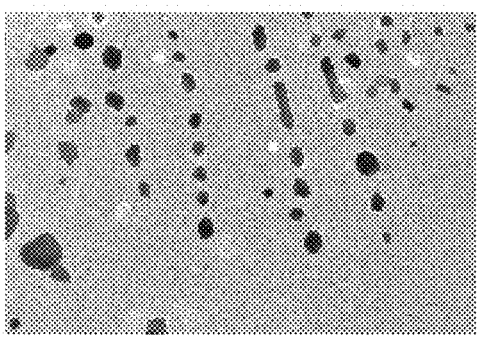

Example 27: Preparation of [Ru(phen)$_2$oBrPIP] (ClO$_4$)$_2$-c-myc Promoter Region DNA Nano-Complex Experimental method: 1 mM [Ru(phen)$_2$oBrPIP](ClO$_4$)$_2$ is uniformly mixed with 1 mM c-myc Pu22 DNA solution in a ratio of 1:1, then the mixture obtained is heated to 90° C. under microwave radiation and maintained at the temperature for 30 seconds to 10 minutes, then the mixture is naturally cooled down to room temperature and left to stand for 24 hours at 4° C. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into an analogous nanotube structure (FIG. 27).

Figure 28:
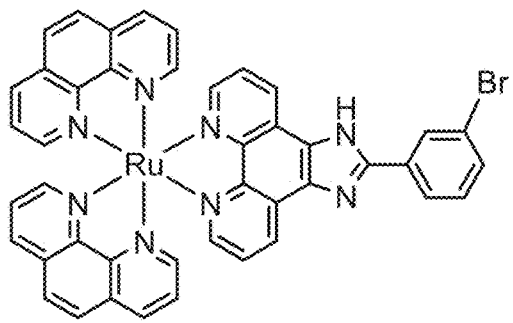
Figure 28:
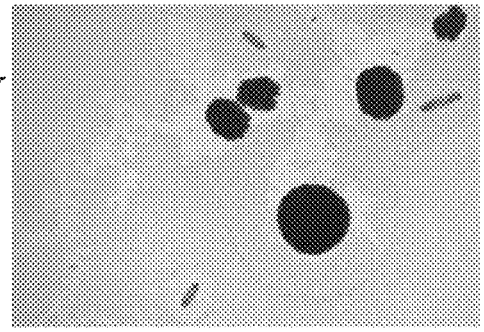

Example 28: Preparation of [Ru(phen)$_2$mBrPIP] (ClO$_4$)$_2$-c-myc Promoter Region DNA Nano-Complex Experimental method: 1 mM [Ru(phen)$_2$mBrPIP](ClO$_4$)$_2$ is uniformly mixed with 1 mM c-myc Pu22 DNA solution in a ratio of 1:1, then the mixture obtained is heated to 90° C. under microwave radiation and maintained at the temperature for 30 seconds to 10 minutes, then the mixture is naturally cooled down to room temperature and left to stand for 24 hours at 4° C. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into an analogous nanotube structure (FIG. 28).

Figure 29:
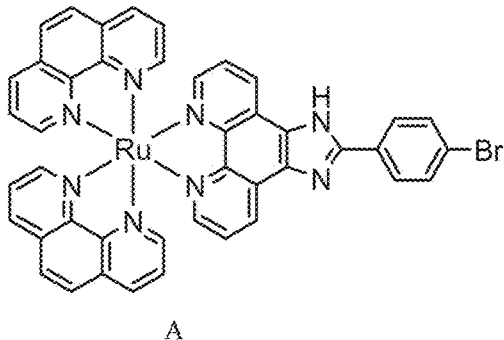
Figure 29:
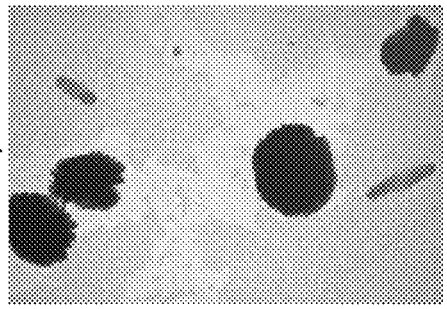

Example 29: Preparation of [Ru(phen)$_2$pBrPIP] (ClO$_4$)$_2$-c-myc Promoter Region DNA Nano-Complex Experimental method: 1 mM [Ru(phen)$_2$pBrPIP](ClO$_4$)$_2$ is uniformly mixed with 1 mM c-myc Pu22 DNA solution in a ratio of 1:1, then the mixture obtained is heated to 90° C. under microwave radiation and maintained at the temperature for 30 seconds to 10 minutes, then the mixture is naturally cooled down to room temperature and left to stand for 24 hours at 4° C. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into an analogous nanotube structure (FIG. 29).

Figure 30:
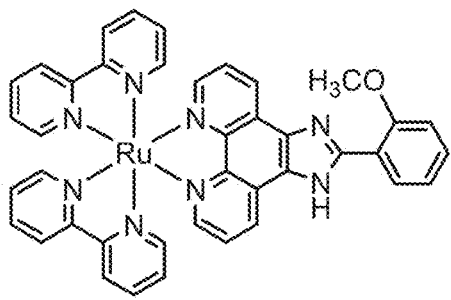
Figure 30:
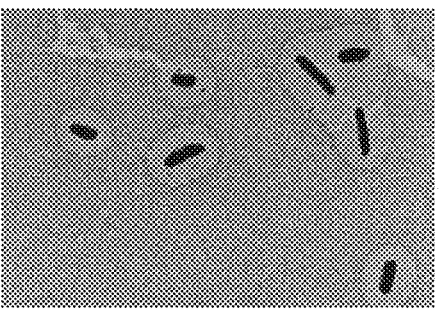

Example 30: Preparation of [Ru(bpy)$_2$oMOPIP] (ClO$_4$)$_2$-c-myc Promoter Region DNA Nano-Complex Experimental method: 1 mM [Ru(bpy)$_2$oMOPIP](ClO$_4$)$_2$ is uniformly mixed with 1 mM c-myc Pu22 DNA solution in a ratio of 1:1, then the mixture obtained is heated to 90° C. under microwave radiation and maintained at the temperature for 30 seconds to 10 minutes, then the mixture is naturally cooled down to room temperature and left to stand for 24 hours at 4° C. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into an analogous nanotube structure (FIG. 30).

Figure 31:
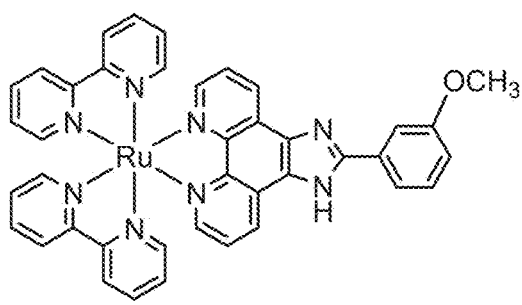
Figure 31:
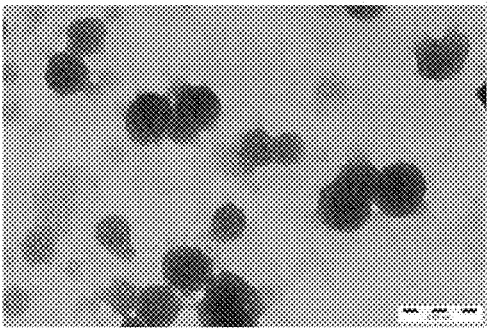

Example 31: Preparation of [Ru(bpy)$_2$mMOPIP] (ClO$_4$)$_2$-c-myc Promoter Region DNA Nano-Complex Experimental method: 1 mM [Ru(bpy)$_2$mMOPIP](ClO$_4$)$_2$ is uniformly mixed with 1 mM c-myc Pu22 DNA solution in a ratio of 1:1, then the mixture obtained is heated to 90° C. under microwave radiation and maintained at the temperature for 30 seconds to 10 minutes, then the mixture is naturally cooled down to room temperature and left to stand for 24 hours at 4° C. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into an analogous nanotube structure (FIG. 31).

Figure 32:
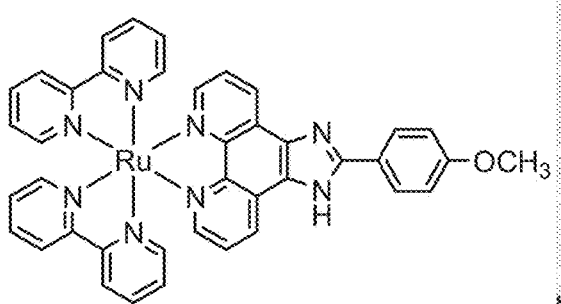
Figure 32:
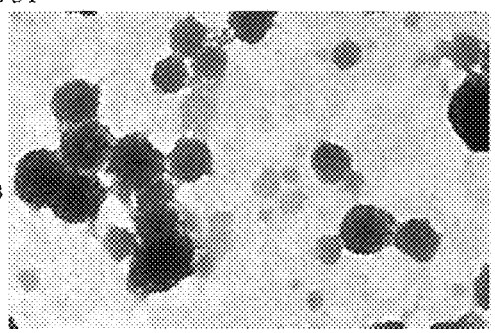

Example 32: Preparation of [Ru(bpy)$_2$pMOPIP] (ClO$_4$)$_2$-c-myc Promoter Region DNA Nano-Complex Experimental method: 1 mM [Ru(bpy)$_2$pMOPIP](ClO$_4$)$_2$ is uniformly mixed with 1 mM c-myc Pu22 DNA solution in a ratio of 1:1, then the mixture obtained is heated to 90° C. under microwave radiation and maintained at the temperature for 30 seconds to 10 minutes, then the mixture is naturally cooled down to room temperature and left to stand for 24 hours at 4° C. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into an analogous nanotube structure (FIG. 32).

Figure 33:
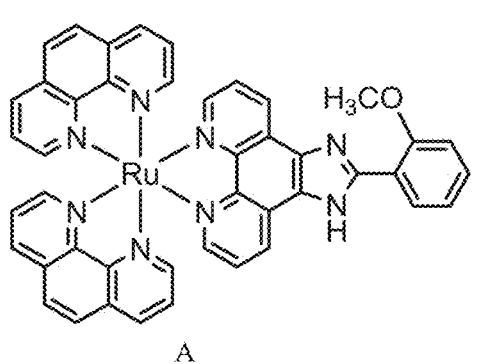
Figure 33:
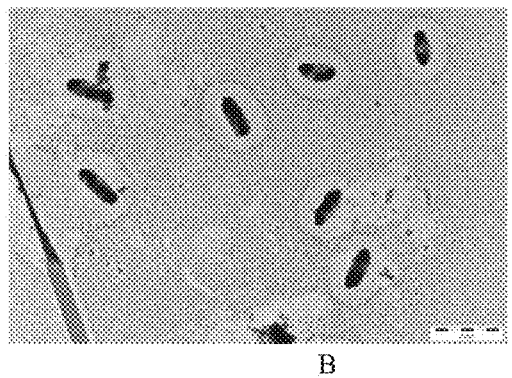

Example 33: Preparation of [Ru(phen)$_2$oMOPIP] (ClO$_4$)$_2$-c-myc Promoter Region DNA Nano-Complex Experimental method: 1 mM [Ru(phen)$_2$oMOPIP](ClO$_4$)$_2$ (FIG. 33A) is uniformly mixed with 1 mM c-myc Pu22 DNA solution in a ratio of 1:1, then the mixture obtained is heated to 90° C. under microwave radiation and maintained at the temperature for 30 seconds to 10 minutes, then the mixture is naturally cooled down to room temperature and left to stand for 24 hours at 4° C. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into an analogous nanotube structure (FIG. 33B).

Figure 34:
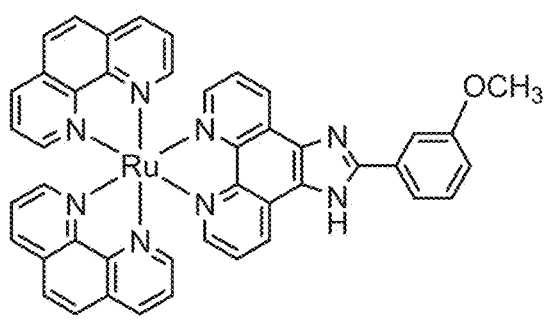
Figure 34:
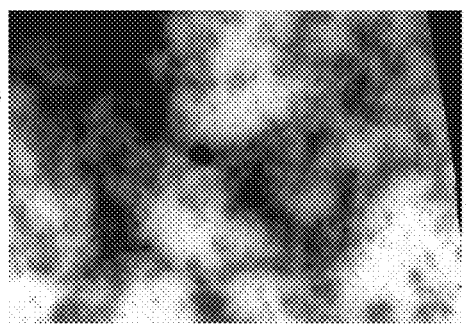

Example 34: Preparation of [Ru(phen)$_2$mMOPIP](ClO$_4$)$_2$-c-myc Promoter Region DNA Nano-Complex Experimental method: 1 mM [Ru(phen)$_2$mMOPIP](ClO$_4$)$_2$ (FIG. 34A) is uniformly mixed with 1 mM c-myc Pu22 DNA solution in a ratio of 1:1, then the mixture obtained is heated to 90° C. under microwave radiation and maintained at the temperature for 30 seconds to 10 minutes, then the mixture is naturally cooled down to room temperature and left to stand for 24 hours at 4° C. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into an analogous nanotube structure (FIG. 34B).

Figure 35:
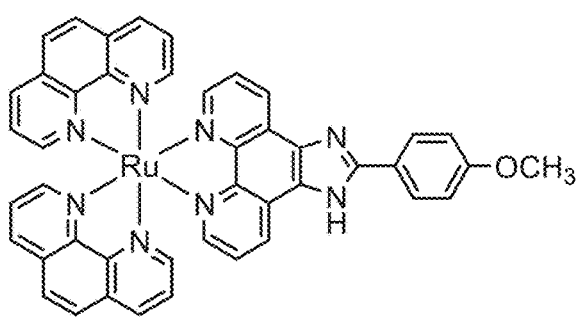
Figure 35:
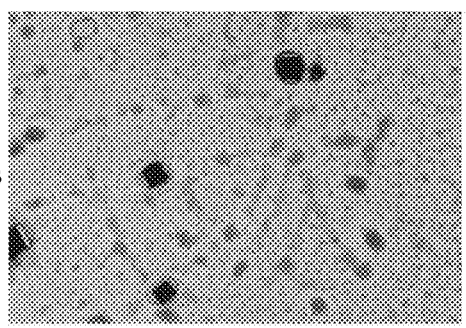

Example 35: Preparation of [Ru(phen)$_2$pMOPIP](ClO$_4$)$_2$-c-myc Promoter Region DNA Nano-Complex Experimental method: 1 mM [Ru(phen)$_2$pMOPIP](ClO$_4$)$_2$ (FIG. 35A) is uniformly mixed with 1 mM c-myc Pu22 DNA solution in a ratio of 1:1, then the mixture obtained is heated to 90° C. under microwave radiation and maintained at the temperature for 30 seconds to 10 minutes, then the mixture is naturally cooled down to room temperature and left to stand for 24 hours at 4° C. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into an analogous nanotube structure (FIG. 35B).

Figure 36:
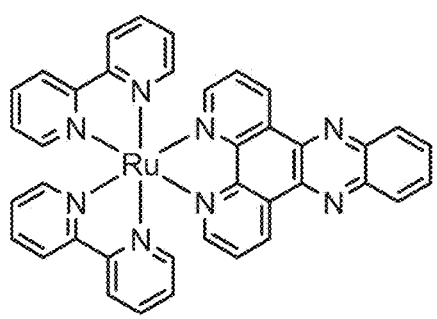
Figure 36:
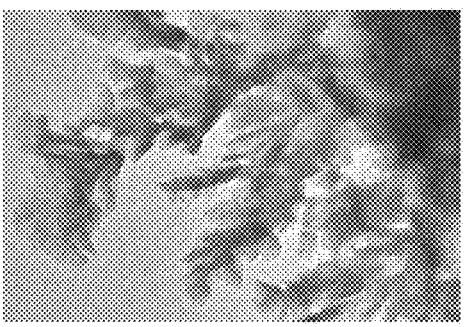

Example 36: Preparation of [Ru(bpy)$_2$DPPZ](ClO$_4$)$_2$-c-myc Promoter Region DNA Nano-Complex Experimental method: 1 mM [Ru(bpy)$_2$DPPZ](ClO$_4$)$_2$ (FIG. 36A) is uniformly mixed with 1 mM c-myc Pu22 DNA solution in a ratio of 1:1, then the mixture obtained is heated to 90° C. under microwave radiation and maintained at the temperature for 30 seconds to 10 minutes, then the mixture is naturally cooled down to room temperature and left to stand for 24 hours at 4° C. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into an analogous nanotube structure (FIG. 36B).

Figure 37:
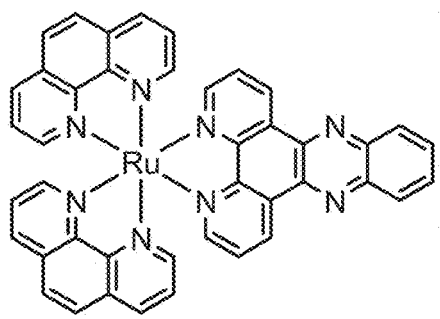
Figure 37:
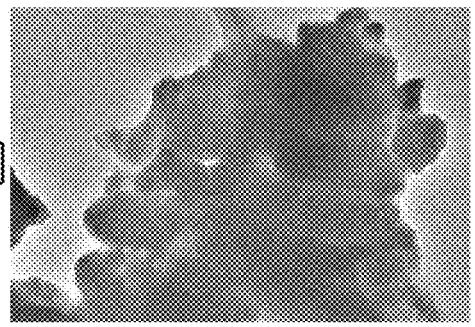

Example 37: Preparation of [Ru(phen)$_2$DPPZ](ClO$_4$)$_2$-c-myc Promoter Region DNA Nano-Complex Experimental method: 1 mM [Ru(phen)$_2$DPPZ](ClO$_4$)$_2$ (FIG. 37A) is uniformly mixed with 1 mM c-myc Pu22 DNA solution in a ratio of 1:1, then the mixture obtained is heated to 90° C. under microwave radiation and maintained at the temperature for 30 seconds to 10 minutes, then the mixture is naturally cooled down to room temperature and left to stand for 24 hours at 4° C. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into an analogous nanotube structure (FIG. 37B).

Figure 38:
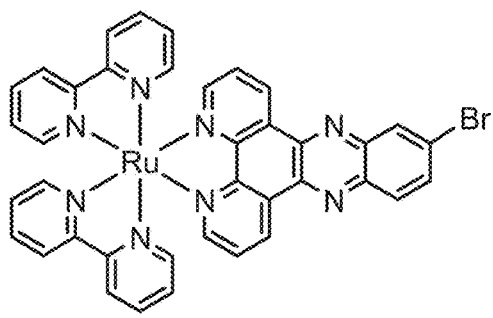
Figure 38:
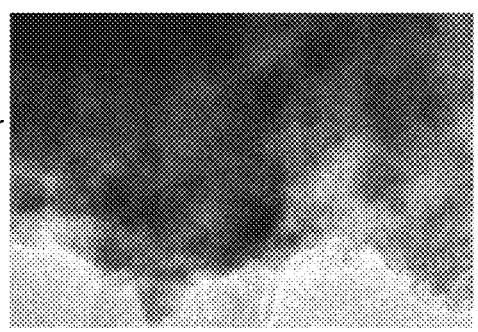

Example 38: Preparation of [Ru(bpy)$_2$3-BrDPPZ](ClO$_4$)$_2$-c-myc Promoter Region DNA Nano-Complex Experimental method: 1 mM [Ru(bpy)$_2$3-BrDPPZ](ClO$_4$)$_2$ (FIG. 38A) is uniformly mixed with 1 mM c-myc Pu22 DNA solution in a ratio of 1:1, then the mixture obtained is heated to 90° C. under microwave radiation and maintained at the temperature for 30 seconds to 10 minutes, then the mixture is naturally cooled down to room temperature and left to stand for 24 hours at 4° C. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into an analogous nanotube structure (FIG. 38B).

Figure 39:
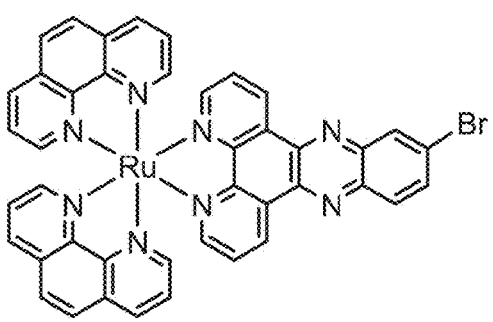
Figure 39:

Example 39: Preparation of [Ru(phen)$_2$3-BrDPPZ](ClO$_4$)$_2$-c-myc Promoter Region DNA Nano-Complex Experimental method: 1 mM [Ru(phen)$_2$3-BrDPPZ](ClO$_4$)$_2$ (FIG. 39A) is uniformly mixed with 1 mM c-myc Pu22 DNA solution in a ratio of 1:1, then the mixture obtained is heated to 90° C. under microwave radiation and maintained at the temperature for 30 seconds to 10 minutes, then the mixture is naturally cooled down to room temperature and left to stand for 24 hours at 4° C. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into an analogous nanotube structure (FIG. 39B).

Figure 40:
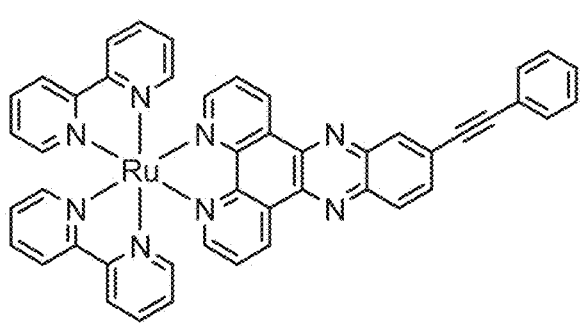
Figure 40:

Example 40: Preparation of [Ru(bpy)$_2$3-BEDPPZ](ClO$_4$)$_2$-c-myc Promoter Region DNA Nano-Complex Experimental method: 1 mM [Ru(bpy)$_2$3-BEDPPZ](ClO$_4$)$_2$ (FIG. 40A) is uniformly mixed with 1 mM c-myc Pu22 DNA solution in a ratio of 1:1, then the mixture obtained is heated to 90° C. under microwave radiation and maintained at the temperature for 30 seconds to 10 minutes, then the mixture is naturally cooled down to room temperature and left to stand for 24 hours at 4° C. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into an analogous nanotube structure (FIG. 40B).

Figure 41:
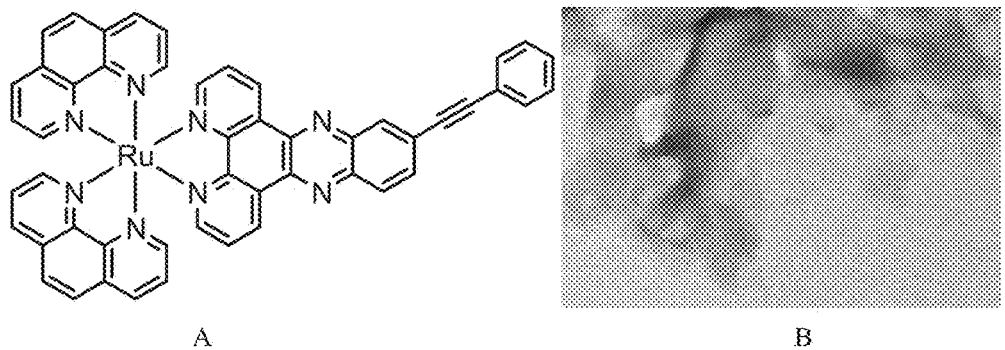

Example 41: Preparation of [Ru(phen)$_2$3-BEDPPZ](ClO$_4$)$_2$-c-myc Promoter Region DNA Nano-Complex Experimental method: 1 mM [Ru(phen)$_2$3-BEDPPZ](ClO$_4$)$_2$ (FIG. 41A) is uniformly mixed with 1 mM c-myc Pu22 DNA solution in a ratio of 1:1, then the mixture obtained is heated to 90° C. under microwave radiation and maintained at the temperature for 30 seconds to 10 minutes, then the mixture is naturally cooled down to room temperature and left to stand for 24 hours at 4° C. The reaction mixture is dialyzed against distilled water to remove the polypyridyl ruthenium (II) complexes unloaded onto the nucleic acid, thereby forming a polypyridyl ruthenium (II) coordination complex-nucleic acid complex. TEM revealed that the ruthenium complex facilitates the telomere DNA sequence to self-assemble into an analogous nanotube structure (FIG. 41B).

Figure 42:
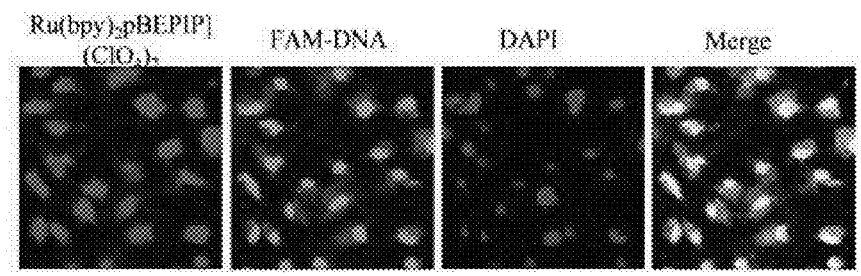
FIG. 42 shows distribution and location of the ruthenium coordination complex-nucleic acid (Fluorescence Activation Microscopy (FAM) fluorescence-labeled) complex (Ru(bpy)$_2$pBEPIP](ClO$_4$)$_2$: FAM-c-myc pu22 DNA=1:1) in hepatic carcinoma HepG2 cells observed under a fluorescence microscope.

Absorption and Distribution of the Nano-complex Formed from Racemic Alkynyl Ruthenium Coordination Complex Ru(bpy)$_2$pBEPIP](ClO$_4$)$_2$ and c-myc DNA (complex of Example 1) for HepG2 Cells Cells in the logarithmic growth phase are seeded in a 2 cm cell culture vessel at a density of $2 \times 10^5$ cells per well. 1 mL DMEM comprising 5 μM ruthenium coordination complex-nucleic acid (FAM fluorescence-labeled) complex (Ru(bpy)$_2$pBEPIP](ClO$_4$)$_2$: FAM-c-myc pu22 DNA=1:1) is added and incubated in a 5% CO$_2$ incubator at 37° C. for 2 hours, then the incubated cells are observed under a fluorescence microscope and the results are shown in FIG. 42. As can be seen from the figure, nucleic acids can be transferred into viable cells via the chiral alkynyl ruthenium complexes and distributed in the whole cells.

Figure 43:
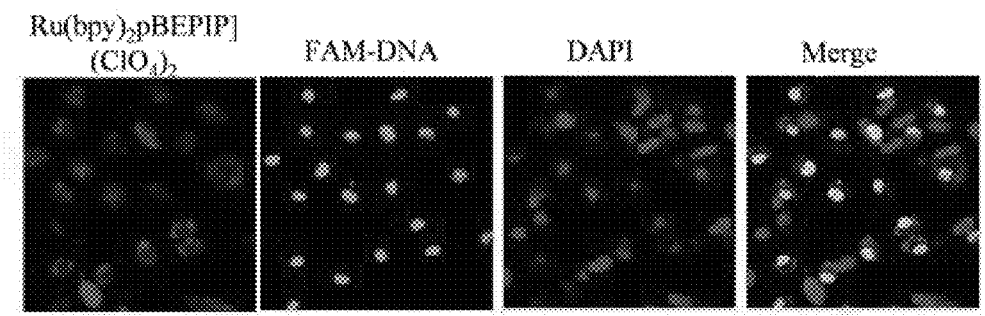
FIG. 43 shows distribution and location of the ruthenium coordination complex-nucleic acid (FAM fluorescence-labeled) complex (Ru(bpy)$_2$pBEPIP](ClO$_4$)$_2$: FAM-c-myc pu22 DNA=1:1) in cervical carcinoma Hela cells observed under a fluorescence microscope.

Absorption and Distribution of the Nano-Complex Formed from Racemic Alkynyl Ruthenium Coordination Complex Ru(Bpy)$_2$pBEPIP](ClO$_4$)$_2$ and c-Myc DNA (Complex of Example 1) for Hela Cells Cells in the logarithmic growth phase are seeded in a 2 cm cell culture vessel at a density of $2 \times 10^5$ cells per well. 1 mL DMEM comprising 5 μM ruthenium coordination complex-nucleic acid (FAM fluorescence-labeled) complex (Ru(bpy)$_2$pBEPIP](ClO$_4$)$_2$: FAM-c-myc pu22 DNA=1:1) is added and incubated in a 5% CO$_2$ incubator at 37° C. for 2 hours, then the incubated cells are observed under a fluorescence microscope and the results are shown in FIG. 43. As can be seen from the figure, nucleic acids can be transferred into viable cells via the racemic alkynyl ruthenium complexes and distributed in the whole cells.

Figure 44:
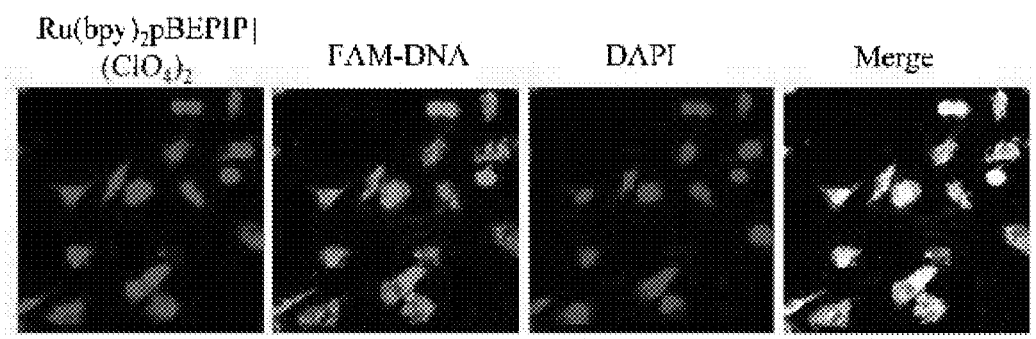
FIG. 44 shows distribution and location of the ruthenium coordination complex-nucleic acid (FAM fluorescence-labeled) complex (Ru(bpy)$_2$pBEPIP](ClO$_4$)$_2$:FAM-c-myc pu22 DNA=1:1) in breast cancer MCF-7 cells observed under a fluorescence microscope.

Absorption and Distribution of the Nano-Complex Formed from Racemic Alkynyl Ruthenium Coordination Complex Ru(Bpy)$_2$pBEPIP](ClO$_4$)$_2$ and c-Myc DNA (Complex of Example 1) for MCF-7 Cells Cells in the logarithmic growth phase are seeded in a 2 cm cell culture vessel at a density of $2 \times 10^5$ cells per well. 1 mL DMEM comprising 5 μM ruthenium coordination complex-nucleic acid (FAM fluorescence-labeled) complex (Ru(bpy)$_2$pBEPIP](ClO$_4$)$_2$: FAM-c-myc pu22 DNA=1:1) is added and incubated in a 5% CO$_2$ incubator at 37° C. for 2 hours, then the incubated cells are observed under a fluorescence microscope and the results are shown in FIG. 44. As can be seen from the figure, nucleic acids can be transferred into a viable cell via the racemic alkynyl ruthenium complexes and distributed in the whole cell.

Figure 45:
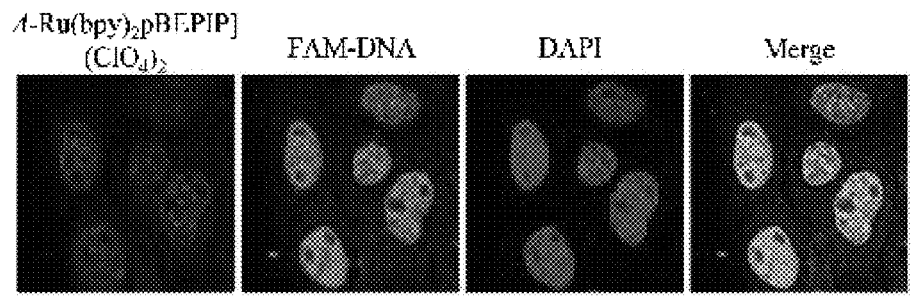
FIG. 45 shows distribution and location of the ruthenium coordination complex-nucleic acid (FAM fluorescence-labeled) complex (Λ-Ru(bpy)$_2$pBEPIP](ClO$_4$)$_2$: FAM-c-myc pu22 DNA=1:1) in hepatic carcinoma HepG2 cells observed under a confocal laser scanning microscope.

Absorption and Distribution of the Nano-Complex Formed from L-Alkynyl Ruthenium Coordination Complex Λ-Ru(Bpy)$_2$pBEPIP](ClO$_4$)$_2$ and c-Myc DNA (Complex of Example 10) for HepG2 Cells Cells in the logarithmic growth phase are seeded in a 2 cm cell culture vessel at a density of $2 \times 10^5$ cells per well. 1 mL DMEM comprising 5 μM ruthenium coordination complex-nucleic acid (FAM fluorescence-labeled) complex Λ-Ru(bpy)$_2$pBEPIP](ClO$_4$)$_2$: FAM-c-myc pu22 DNA=1:1) is added and incubated in a 5% CO$_2$ incubator at 37° C. for 2 hours, then the incubated cells are observed under a fluorescence microscope and the results are shown in FIG. 45. As can be seen from the figure, nucleic acids can be transferred into a viable cell via the L-alkynyl ruthenium complexes and distributed in the cell nucleus.

Figure 46:
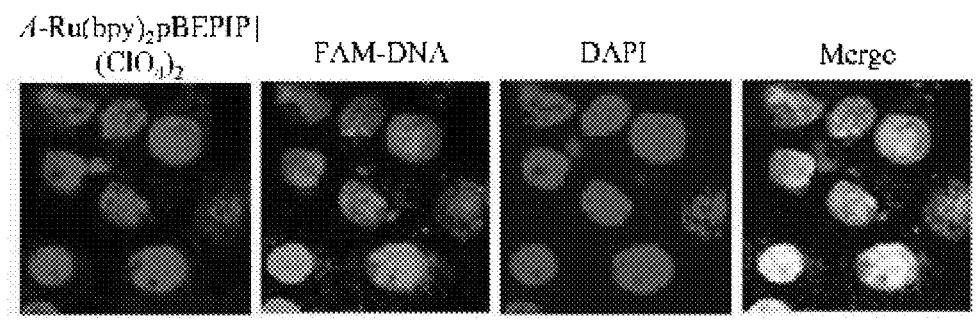
FIG. 46 shows distribution and location of the ruthenium coordination complex-nucleic acid (FAM fluorescence-labeled) complex (Λ-Ru(bpy)$_2$pBEPIP](ClO$_4$)$_2$:FAM-c-myc pu22 DNA=1:1) in hepatic carcinoma MCF-7 cells observed under a confocal laser scanning microscope.

Absorption and Distribution of the Nano-Complex Formed from L-Alkynyl Ruthenium Coordination Complex Λ-Ru(Bpy)$_2$BEPIP](ClO$_4$)$_2$ and c-Myc DNA (Complex of Example 10) for MCF-7 Cells Cells in the logarithmic growth phase are seeded in a 2 cm cell culture vessel at a density of $2 \times 10^5$ cells per well. 1 mL DMEM comprising 5 μM ruthenium coordination complex-nucleic acid (FAM fluorescence-labeled) complex Λ-Ru(bpy)$_2$pBEPIP](ClO$_4$)$_2$: FAM-c-myc pu22 DNA=1:1) is added and incubated in a 5% CO$_2$ incubator at 37° C. for 2 hours, then the incubated cells are observed under a fluorescence microscope and the results are shown in FIG. 46. As can be seen from the figure, nucleic acids can be transferred into a viable cell via the L-alkynyl ruthenium complexes and distributed in the cell nucleus.

Figure 47:
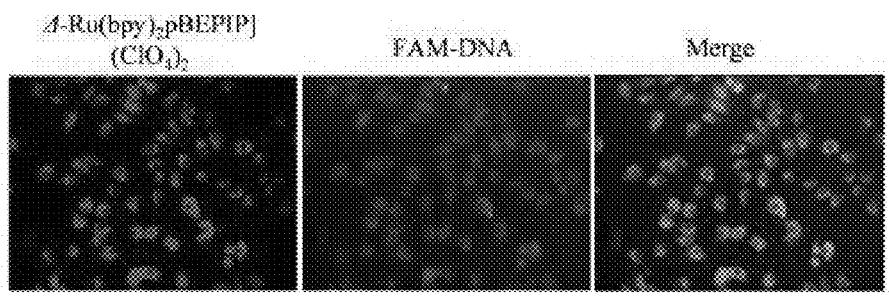
FIG. 47 shows distribution and location of the ruthenium coordination complex-nucleic acid (FAM fluorescence-labeled) complex (Δ-Ru(bpy)$_2$pBEPIP](ClO$_4$)$_2$: FAM-c-myc pu22 DNA=1:1) in hepatic carcinoma HepG2 cells observed under a fluorescence microscope.

Absorption and Distribution of the Nano-Complex Formed from R-Alkynyl Ruthenium Coordination Complex Δ-Ru(Bpy)$_2$pBEPIP](ClO$_4$)$_2$ and c-Myc DNA (Complex of Example 11) for HepG2 Cells Cells in the logarithmic growth phase are seeded in a 2 cm cell culture vessel at a density of $2 \times 10^5$ cells per well. 1 mL DMEM comprising 5 μM ruthenium coordination complex-nucleic acid (FAM fluorescence-labeled) complex Δ-Ru(bpy)$_2$pBEPIP](ClO$_4$)$_2$: FAM-c-myc pu22 DNA=1:1) is added and incubated in a 5% CO$_2$ incubator at 37° C. for 2 hours, then the incubated cells are observed under a fluorescence microscope and the results are shown in FIG. 47. As can be seen from the figure, nucleic acids can be transferred into a viable cell via the R-alkynyl ruthenium complexes and distributed in the cytoplasm.

Figure 48:
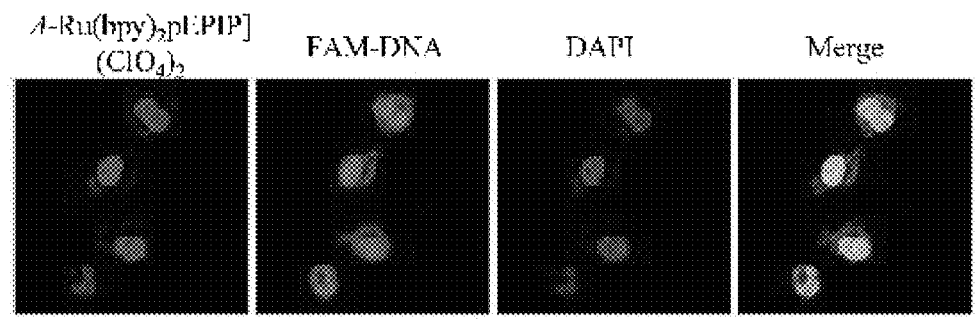
FIG. 48 shows distribution and location of the ruthenium coordination complex-nucleic acid (FAM fluorescence-labeled) complex (Λ-Ru(bpy)$_2$pEPIP](ClO$_4$)$_2$: FAM-AS1411 DNA=1:1) in hepatic carcinoma HepG2 cells observed under a fluorescence microscope.

Absorption and Distribution of the Nano-Complex Formed from L-Alkynyl Ruthenium Coordination Complex Λ-Ru(Bpy)$_2$pBEPIP](ClO$_4$)$_2$ and AS1411 DNA (Complex of Example 11) for MCF-7 Cells Cells in the logarithmic growth phase are seeded in a 2 cm cell culture vessel at a density of $2 \times 10^5$ cells per well. 1 mL DMEM comprising 5 μM ruthenium coordination complex-nucleic acid (FAM fluorescence-labeled) complex Δ-Ru(bpy)$_2$pBEPIP](ClO$_4$)$_2$: FAM-AS1411 DNA=1:1) is added and incubated in a 5% CO$_2$ incubator at 37° C. for 2 hours, then the incubated cells are observed under a fluorescence microscope and the results are shown in FIG. 48. As can be seen from the figure, nucleic acids can be transferred into a viable cell via the R-alkynyl ruthenium complexes and distributed in the cell nucleus.

The invention claimed is:

1. A ruthenium complex for nucleic acid sequence vector application, the ruthenium complex has the following general formula:

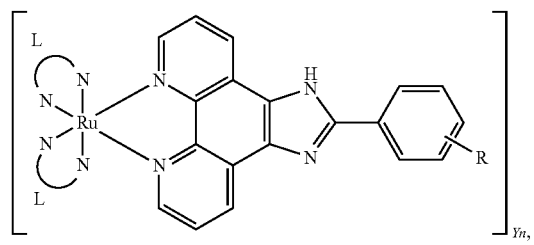

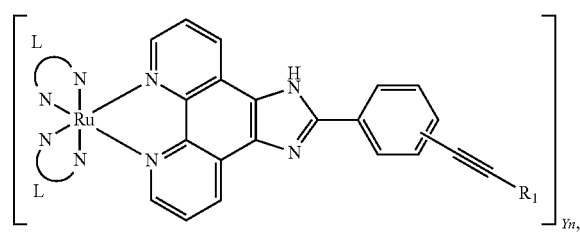

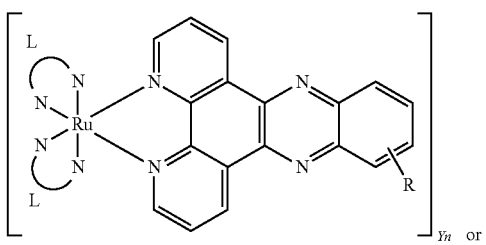

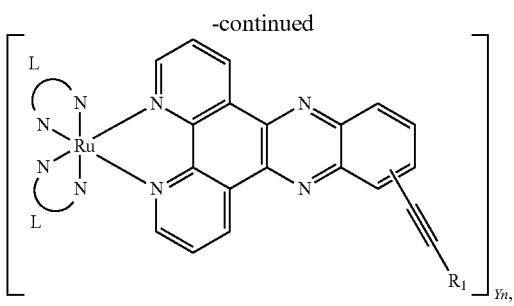

wherein:

L is an auxiliary ligand having a structural formula of:

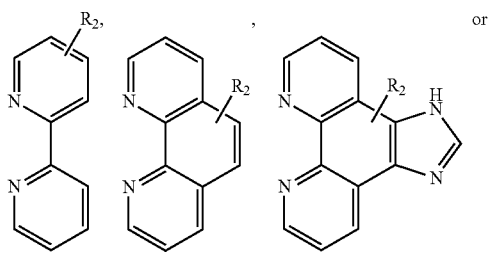

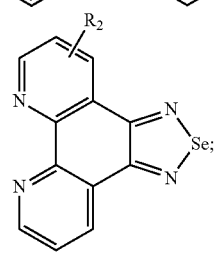

R is independently selected from substituted alkyl, substituted phenyl, substituted pyridyl, substituted furyl, substituted thiazole and substituted pyrrole, wherein substituted group is selected from hydroxyl, nitro, halogen, amino, carboxy, cyano, mercapto, $C_3$-$C_8$ cycloalkyl, $SO_3H$, $C_1$-$C_6$ alkyl, $C_2$-$C_6$ alkenyl, $C_2$-$C_6$ alkynyl, hydroxyl($C_1$-$C_6$)alkyl, amino($C_1$-$C_6$)alkyl, $CO_2R'$, $CONR'R'$, $COR'$, $SO_2R'R'$, ($C_1$-$C_6$)alkoxyl, ($C_1$-$C_6$)alkylsulphide, —N=NR', NR'R' or trifluoro ($C_1$-$C_6$)alkyl; wherein R' is selected from H, $C_1$-$C_6$ alkyl or phenyl;

$R_1$ is independently selected from hydrogen, hydroxyl, trimethylsilyl, $C_1$-$C_6$ alkyl or substituted $C_1$-$C_6$ alkyl, phenyl or substituted phenyl, pyridyl or substituted pyridyl, furyl or substituted furyl, pyrryl or substituted pyrryl, thiazolyl or substituted thiazolyl; wherein the position of $R_1$ substituted ethynyl may be ortho-position, meta-position or para-position on the benzene ring; the number of substituted ethynyl is 1, 2 or more;

$R_2$ is independently selected from methyl, methoxyl, nitro and halogen;

Y is an ion or acidic radical ion which makes the whole ruthenium(II) complex electrically neutral, n is the number of ions or acidic radical ions which makes the whole ruthenium(II) complex electrically neutral;

the nucleic acid sequence has a length of at least 4 bp.

2. The ruthenium complex according to claim 1, characterized in that the ruthenium complex is selected from:

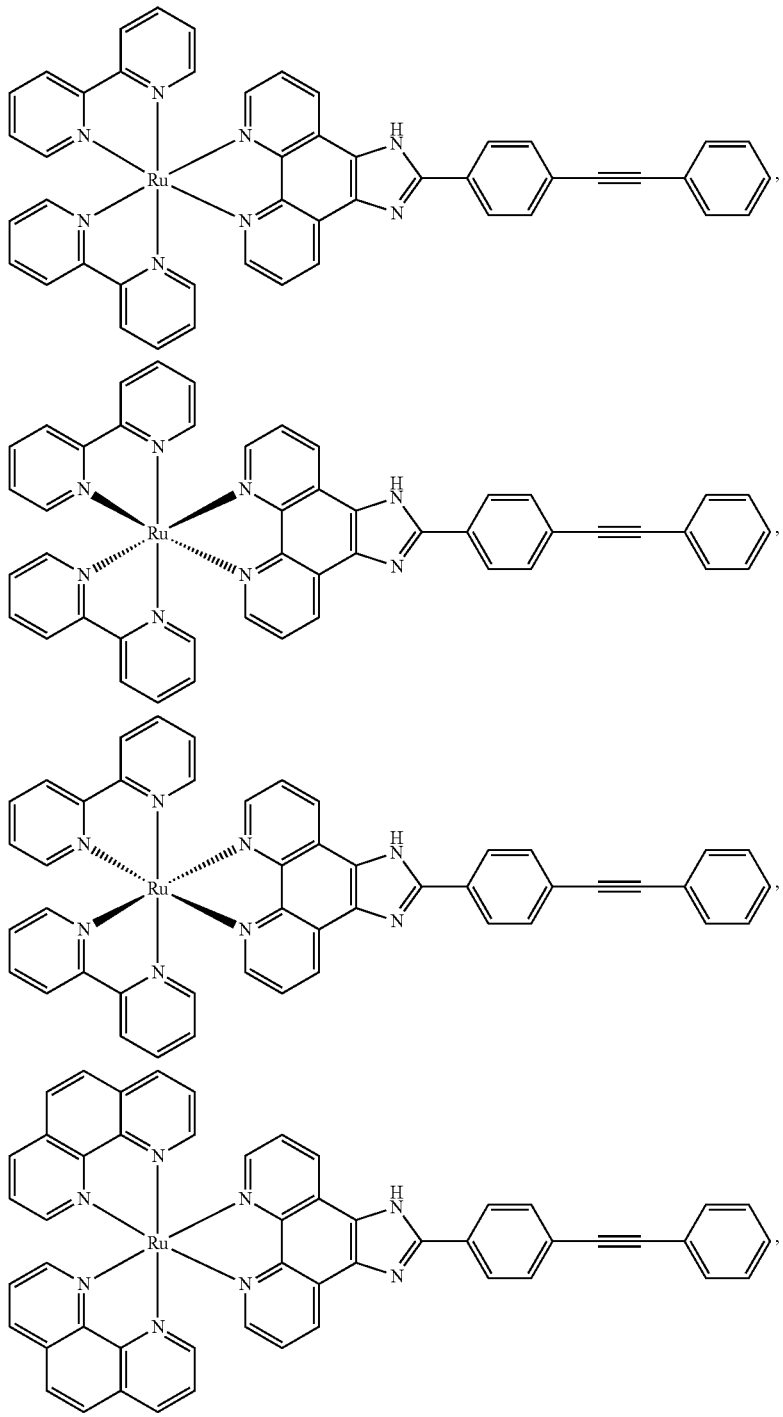

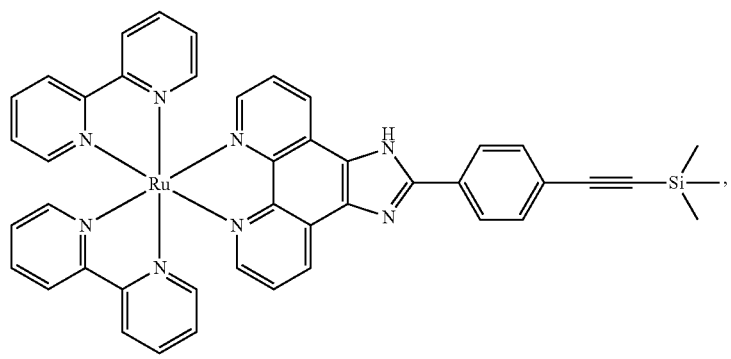
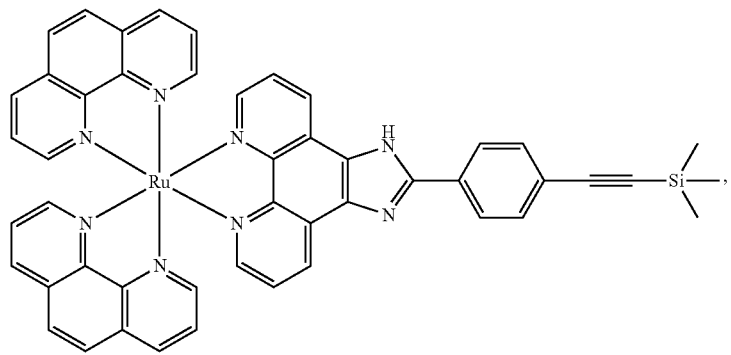
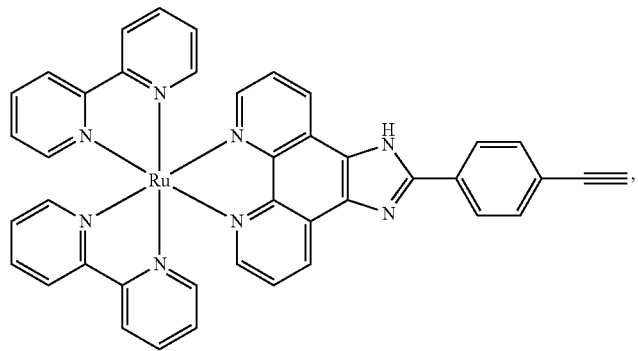
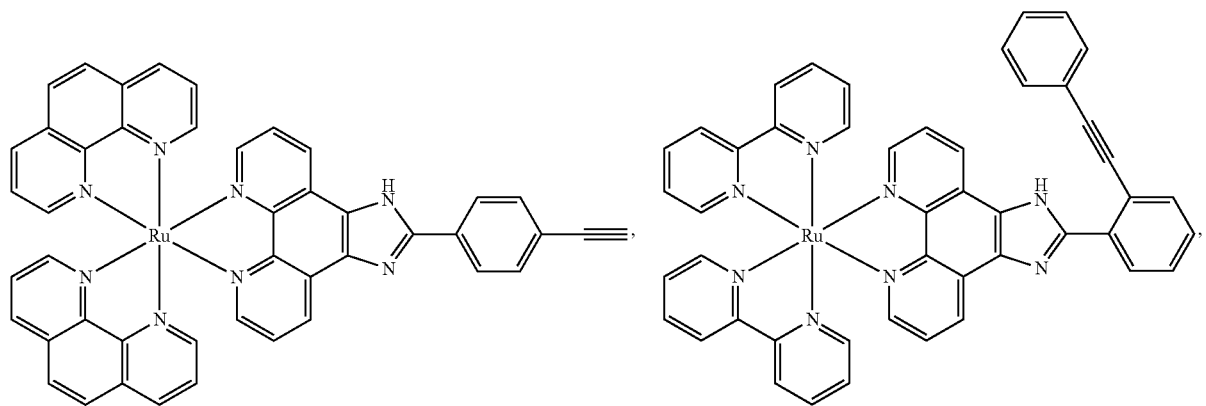

-continued
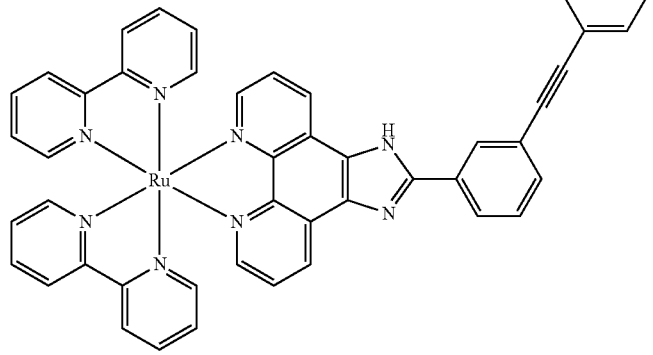
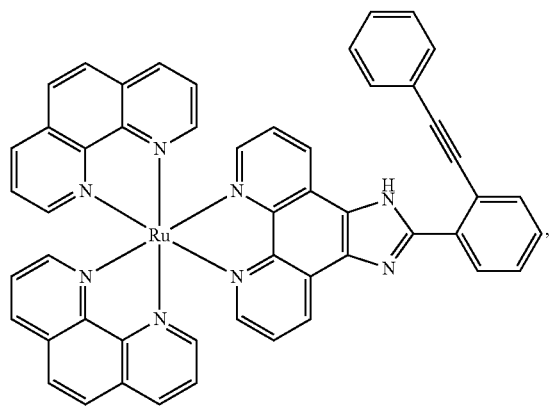
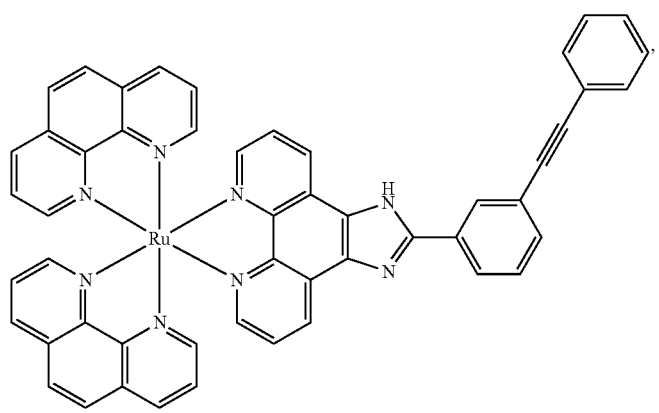
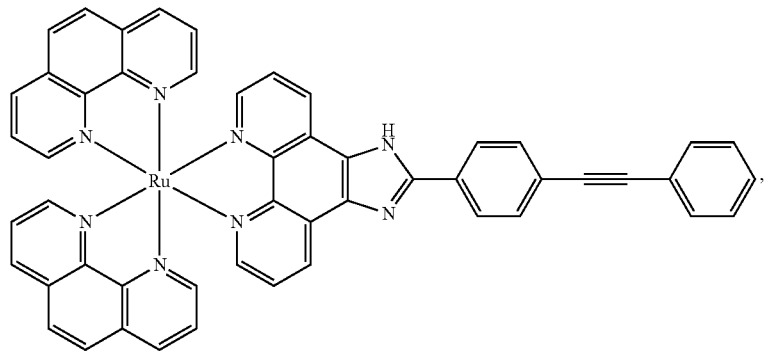

41
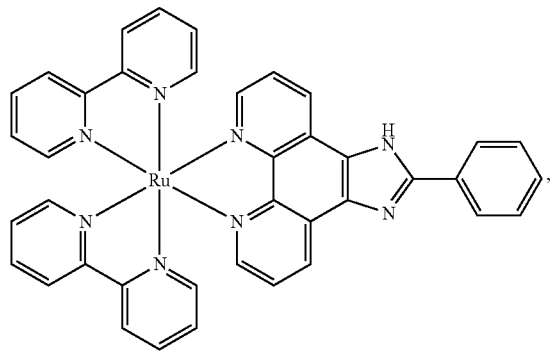
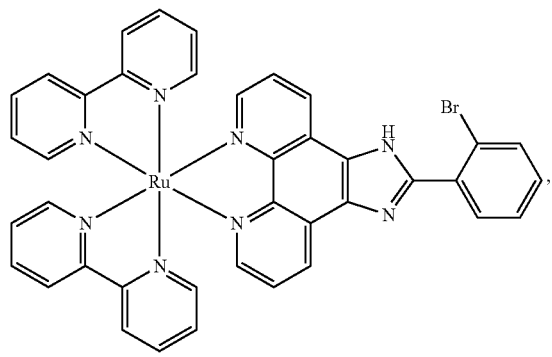
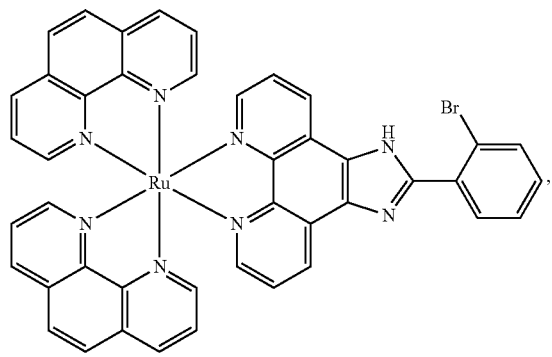
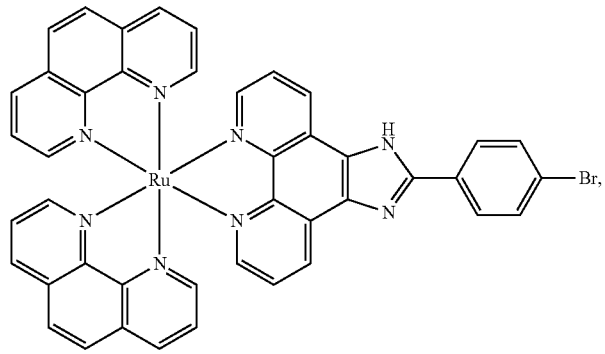
42
-continued
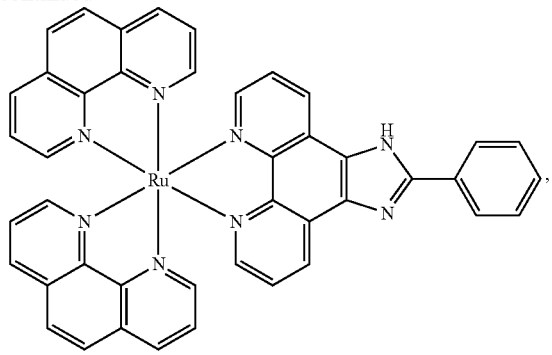
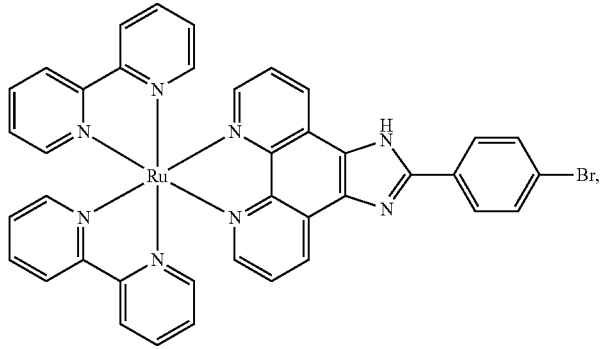
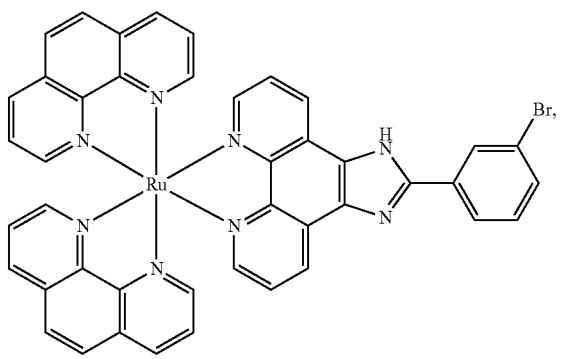
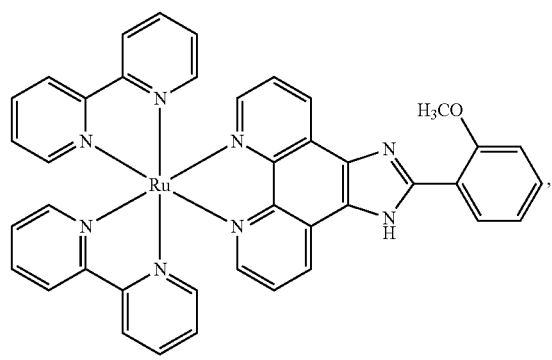

-continued
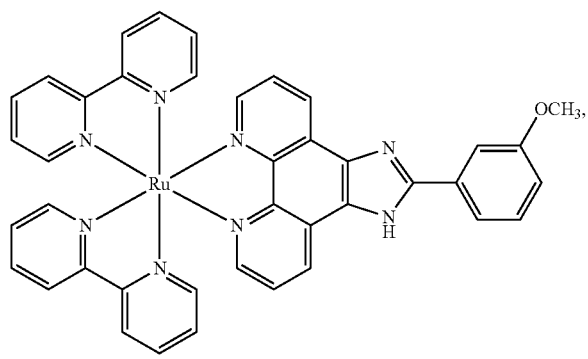
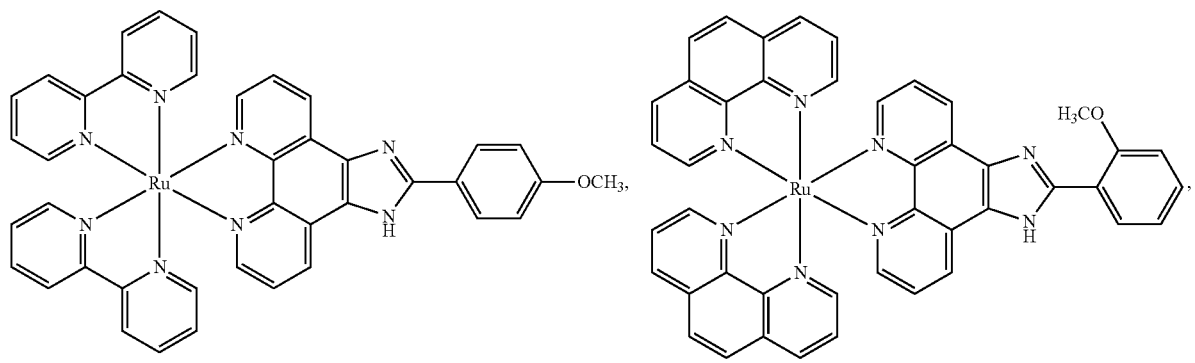
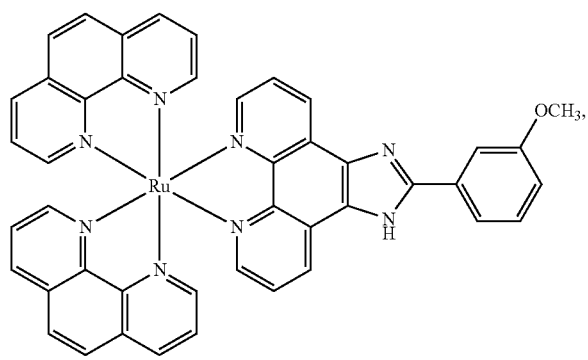
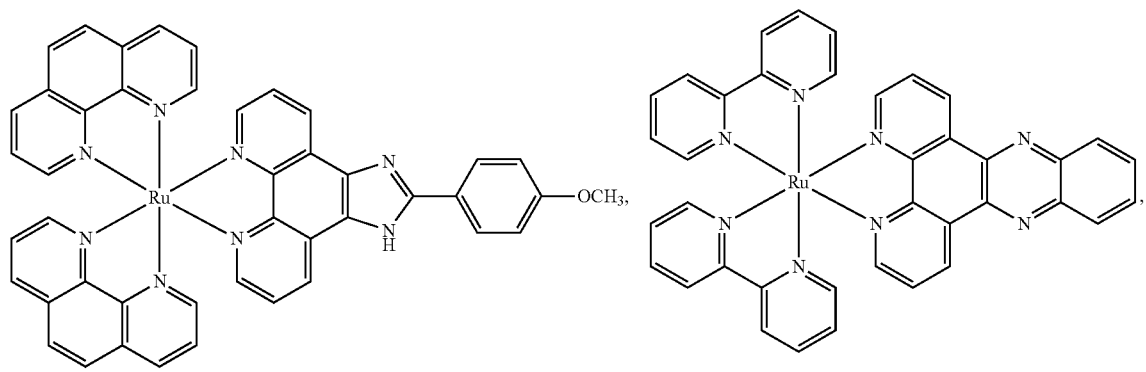

-continued

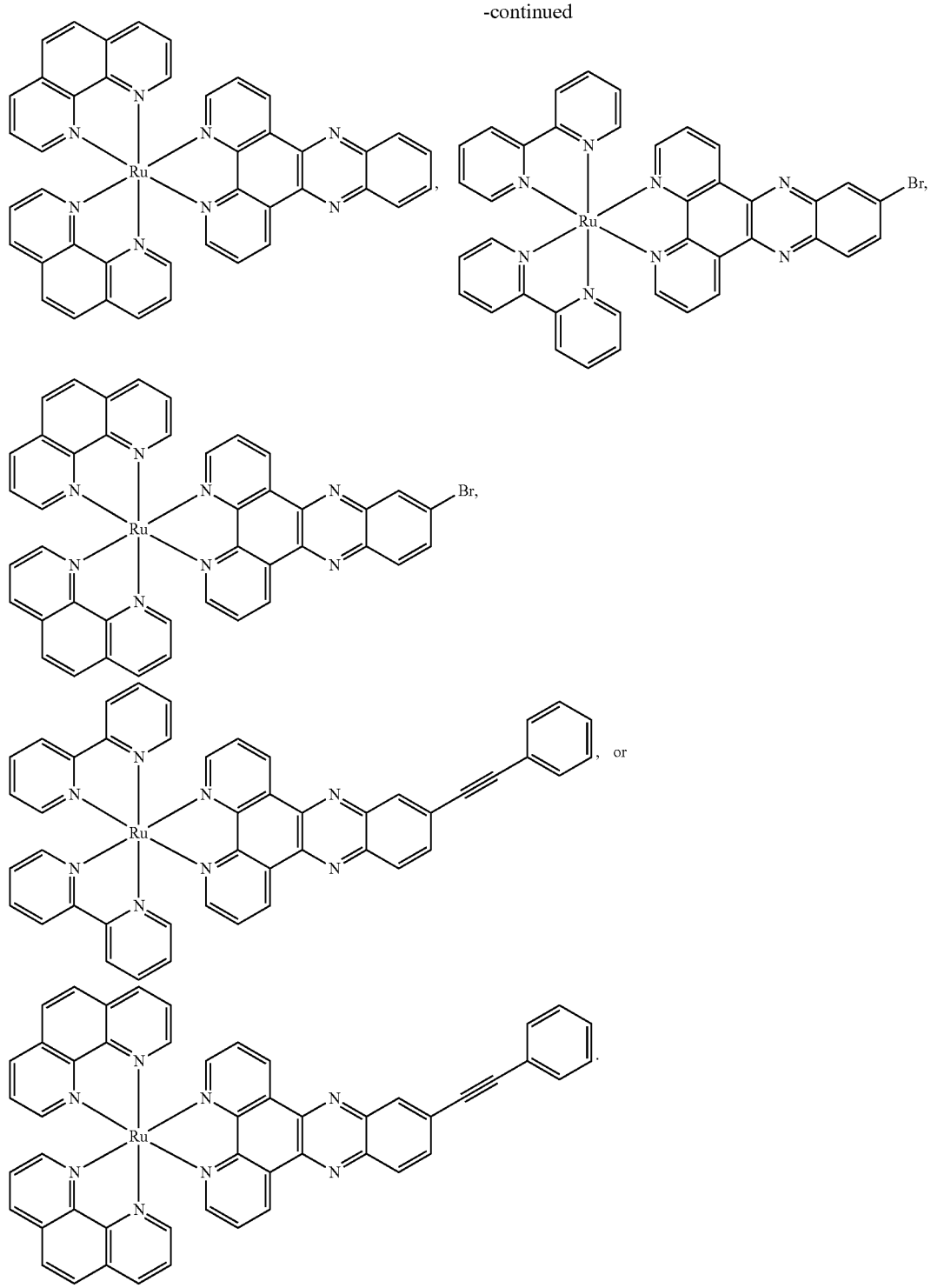

3. The ruthenium complex according to claim 1, characterized in that the ruthenium complex is a single chiral isomer thereof.

4. The ruthenium complex according to claim 1, characterized in that the length of the nucleic acid sequence is not longer than 3,000 bp.

5. The ruthenium complex according to claim 1, characterized in that the nucleic acid is a fluorophore-labeled nucleic acid.

6. The ruthenium complex according to claim 1, characterized in that the nucleic acid sequence is selected from c-myc promoter region DNA, C-kit promoter region DNA, bcl-2 promoter region DNA, miR-21, DNA of AS1411, siRNA, microRNA, aptamer and mRNA.

7. A fluorescent probe comprising:
a ruthenium coordination complex; and
a nucleic acid sequence, wherein the ruthenium complex is as claimed in claim 1.

8. The fluorescent probe according to claim 7, characterized in that the fluorescent probe is prepared by the following steps:
- uniformly mixing a ruthenium complex with a nucleic acid solution to obtain a mixture;
- then heating the mixture obtained to a temperature ranging from 70° C. to 100° C.;
- maintaining the temperature for 30 seconds to 30 minutes;
- cooling the mixture; and
- removing free ruthenium complexes after cooling to form a ruthenium coordination complex-nucleic acid complex;
- wherein the ruthenium complex has a structural formula according to claim 1 and the nucleic acid has a length that is not shorter than 4 bp.

9. The fluorescent probe according to claim 8, characterized in that the nucleic acid is a fluorophore-labeled nucleic acid.

10. The fluorescent probe according to claim 8, characterized in that the heating is performed by a microwave.

11. The ruthenium complex according to claim 2, characterized in that the ruthenium complex is a single chiral isomer thereof.

12. The fluorescent probe according to claim 4, characterized in that the nucleic acid is a fluorophore-labeled nucleic acid.

13. The fluorescent probe according to claim 7, characterized in that the fluorescent probe is prepared by the following steps:
- uniformly mixing a ruthenium complex with a nucleic acid solution to obtain a mixture;
- then heating the mixture obtained to a temperature ranging from 70° C. to 100° C.;
- maintaining the temperature for 30 seconds to 30 minutes;
- cooling the mixture; and
- removing free ruthenium complexes after cooling to form a ruthenium coordination complex-nucleic acid complex;
- wherein the ruthenium complex has a structural formula according to claim 2 and the nucleic acid has a length that is not shorter than 4 bp.

14. The fluorescent probe according to claim 7, characterized in that the fluorescent probe is prepared by the following steps:
- uniformly mixing a ruthenium complex with a nucleic acid solution to obtain a mixture;
- then heating the mixture obtained to a temperature ranging from 70° C. to 100° C.;
- maintaining the temperature for 30 seconds to 30 minutes;
- cooling the mixture; and
- removing free ruthenium complexes after cooling to form a ruthenium coordination complex-nucleic acid complex;
- wherein the ruthenium complex has a structural formula according to claim 3 and the nucleic acid has a length that is not shorter than 4 bp.

* * * * *